United States Patent [19]

Andersson et al.

[11] Patent Number: 5,398,885
[45] Date of Patent: Mar. 21, 1995

[54] DISCRETE DISTRIBUTED SENSORS AND SYSTEM FOR SPATIAL SENSING

[75] Inventors: Mark S. Andersson; Edward F. Crawley, both of Cambridge, Mass.

[73] Assignee: Massachusetts Institute of Technology, Cambridge, Mass.

[21] Appl. No.: 975,510

[22] Filed: Nov. 12, 1992

[51] Int. Cl.⁶ .................. G01N 29/04; G01L 9/00
[52] U.S. Cl. .................. 244/1 R; 73/DIG. 4; 73/180; 73/147; 73/774; 73/862.623; 73/754; 244/203; 244/219; 244/75 R; 244/76 R
[58] Field of Search ............ 244/203, 219, 218, 75 R, 244/76 R, 194, 195; 73/180, 147, 774-777, 862.473, 862.474, 862.623, 862.626, 862.627, 862.629, DIG. 4; 310/322, 328

[56] References Cited

U.S. PATENT DOCUMENTS

| | | | |
|---|---|---|---|
| 4,485,321 | 11/1984 | Klicker et al. | 73/DIG. 4 |
| 4,725,020 | 2/1988 | Whitever | 244/76 R |
| 4,868,447 | 9/1989 | Lee et al. | 310/328 |
| 5,054,323 | 10/1991 | Hubbard et al. | 73/DIG. 4 |

FOREIGN PATENT DOCUMENTS 1228007 4/1986 U.S.S.R. .................. 73/DIG. 4

OTHER PUBLICATIONS

Andersson, et al., "Discrete Shaped Strain Sensors For Intelligent Structures", Space Engineering Research Center, Massachusetts Institute of Technology, Cambridge, Mass. 02139, Submitted to the 2nd U.S./Japan Conference on Adaptive Structures, Nov. 12-14, 1991.
Andersson, et al. "Discrete Distributed Strain Sensing of Intelligent Structures", Space Engineering Research Center, Massachusetts Institute of Technology, Cambridge, Mass. 02139, Presented at the 33rd SDM Conference, Dalls, Tex. Apr. 13-15, 1992.
Crawley, et al. "Static Aeroelastic Control Using Strain Actuated Adaptive Structures", Space Engineering Research Center Department of Aeronautic and Astronautics, Masschusetts Institute of Technology, Cambridge, Mass. 02139, Submitted to the U.S./Japan Conference on Adaptive Structures Nov. 13, 1990.

Primary Examiner—Galen L. Barefoot
Attorney, Agent, or Firm—Thomas J. Engellenner; Michael I. Falkoff

[57] ABSTRACT

A sensor has a sensing region that responds to a surface property by producing an output signal. The sensor has a spatially distributed shape or sensitivity so that the output decreases away from a central part of the sensor, and thus the outputs of plural sensors combined have finite spatial transform as well as high roll off in spatial frequency. Preferably the output decreases to zero at edges of the sensor, and conditions of continuity or vanishing may be imposed on first or higher order derivatives. An edge sensor suitable for mounting at the edge of the structure has its weight function obtained by processes of reflecting and inverting the weight function at an edge. A sensor system employs plural such sensors and edge sensors to produce bounded spatial transfer functions for characterizing the structure. Embodiments of piezoelectric, resistive, capacitive and thermal sensors are described.

15 Claims, 20 Drawing Sheets

FIGURE 13A  Wavenumber ratio k/ko

Wavenumber ratio k/ko

FIGURE 17A  Wavenumber ratio k/ko

Wavenumber ratio k/ko

FIGURE 18A  Wavenumber ratio k/ko

FIGURE 19A    Wavenumber ratio k/ko

FIGURE 20A    Wavenumber ratio k/ko

FIGURE 21A  Wavenumber ratio k/ko

Wavenumber ratio k/ko

DISCRETE DISTRIBUTED SENSORS AND SYSTEM FOR SPATIAL SENSING

This invention was made with government support under Contract Number F49620-92-J-0010 awarded by the Air Force. The government has certain rights in the invention.

BACKGROUND OF THE INVENTION

This invention relates to the field of intelligent structures, i.e., structures which have sensing, processing and actuator mechanisms built in to change in response to evolving dynamic conditions or states of the structure.

An ideal intelligent structure would incorporate sets of highly distributed actuators, sensors and processors. Much work to date has centered on the development of technology for distributed actuators. However, less work has been performed on distributed sensors, and only a few pioneering efforts have dealt with distributed processors. All three of these components should be present in a system in order to implement a closed-loop shape control scheme of any complexity. The need for additional work on sensors specifically useful for intelligent structures has motivated the present invention.

The use of piezoelectric materials in intelligent structures has been studied by de Luis and by Anderson. De Luis et al. developed analytical models of piezoelectric actuators for intelligent structures, and verified these models experimentally. Analytic models were developed for static and dynamic actuation of segments of piezoelectric material either embedded in a structure or bonded to its surface. These models allow the response of the structure to actuation of the piezoelectrics to be predicted, and therefore help in efficient or optimal actuator placement. De Luis showed that although the stiffness of the structure is not strongly affected by the addition of embedded piezoelectric components, the ultimate strength of the structure is reduced. Anderson et al. also develop models for induced-strain actuation of beam-like structures. Two analytical models and one finite element based model were presented to model extension, bending and shearing deformations. In addition to this work on piezoelectric materials, electrostrictive and magnetostrictive materials as well as shape memory alloys have been investigated.

Some work has been done by Warkentin et al. on integrating electronic components in intelligent structures, who demonstrated that embedding processing and other electronic components in addition to sensors and actuators within an intelligent structure simplifies physical implementation. They described a technique for embedding silicon chips within the plies of a graphite/epoxy composite laminated structure.

Control schemes suitable for implementation on structures containing distributed actuators, sensors and processors have been developed by de Luis and by How. De Luis et al. developed optimal controllers for intelligent structures by assuming that the sensors and actuators are so numerous that they may be considered spatially continuous. This allowed use of a functional analysis approach to derive control algorithms to which an experimental implementation of a prototype of an intelligent structure and optimal controllers were derived and implemented. How et al., on the other hand, presented a new control architecture specially suited to intelligent structures with many distributed sensors and actuators. This architecture is a hierarchic one with many controllers operating at a local level, and a single global one operating to control overall motions of the flexible structure.

In the area of sensors, work at the Massachusetts Institute of Technology has been done on a variety of modal, convolving and wave sensors. Collins et al. have developed piezoelectric film sensors for the control of a two-link planar flexible robotic manipulator system. The spatial shape of the sensors is selected such that their output is proportional to a mode of the structure. These sensors make it possible to directly measure particular dynamic states of a flexible structure. Otherwise, such states would have to be determined using an estimator and some inherently inaccurate analytical model of the structure. Miller et al. investigated sensors which output a single temporal signal by convolving measurements of structural variables distributed over a finite length of a structure. The shape of the sensor determines how this convolution procedure takes place. This shape can be optimized to ensure that the sensor is specially suited for use in the control of flexible structures, because it can be designed such that the sensor output rolls off without exhibiting phase lag relative to a point sensor at its center. This would allow gain stabilization without the accompanying reduction of available gain margin.

Lee et al. have also worked on modal sensors as well as actuators. Lee and Moon developed a theory for sensing and actuation in piezoelectric laminates, in order to develop modal sensors and actuators. Such sensors, designed for one-dimensional operation have been modeled analytically and compared to experimental implementations. If such sensors were manufactured accurately, actuator or observer spillover would not exist and the modal coordinates of a structure could theoretically be measured or actuated directly. Lee, Chiang and O'Sullivan constructed modal sensors and actuators to critically damp a cantilever plate using PVF2 piezoelectric film. Using plate theory extended to include piezoelectric actuators and sensors. The sensor geometry was designed such that the sensor signal is proportional to the derivative in time of the modal coordinate of the structure. This allows a simple derivative feedback controller to be implemented. They showed that critical damping can be achieved using this controller.

A principal advantage of such shape sensors is that, relative to a point sensor at their center, they allow a rolloff in amplitude of measurement output without a change in phase. The rolloff of such sensors is not limited by Bode's Gain-Phase Theorem, because the sensors doe not make causal measurements. Bode's integral defines a relationship between the magnitude and phase of a dynamic system. The integral holds only for causal dynamics and requires that any magnitude rolloff must be accompanied by some phase lag. Point sensors are limited by Bode's theorem because they are causal and only measure present information. However, any sensor measuring strain over a finite length has access to incoming waves (future information) and outgoing waves (past information) at the same instant. Thus it has information which is noncausal with respect to its midpoint: it can sense future events. This enables it to exhibit magnitude rolloff with no associated phase lag. In the abstract, this property offers great potential for control systems based on shape sensors.

One of the shortcomings of work done to date on modal sensors is the fact that, to work well, the sensors must be able to sense deformations from all or large parts of the structure. This means that the sensor must cover a large fraction of the structure. It becomes problematic to implement several modal sensors on the same structure. Another problem is that modal sensors are typically implemented in hardware. This means that the output properties of the sensors as a function of frequency are constant. Therefore, should the shape or mass of the structure change, the mode shapes will change, and the modal sensors will not operate correctly. A third problem with the sensors currently being investigated is that it is problematic to extrapolate their design to more complex structures, such as truss structures or two-dimensional plate-like structures.

Accordingly it is desirable to develop techniques for the design of discrete distributed sensor systems that accurately estimate the quasistatic and dynamic states of an intelligent structure in a manner suitable for closed-loop control or identification.

SUMMARY AND OBJECTS OF THE INVENTION

It is an object of the invention to provide sensors for a distributed sensor system for estimating the global shape or other physical state of a structure.

Ancillary objects include those which involve the properties of individual sensors; those which involve the properties of the system of discrete distributed sensors as a whole; and those which relate to practical implementation.

As regards the individual sensors:

1. Individual sensors should be able to accurately observe and precisely resolve modes which are targeted for control.

2. The observability of the dynamic modes should roll off quickly in frequency beyond the desired bandwidth.

3. The transfer function from the strain at the center of the sensor to the sensor output, as a function of spatial frequency, should not contain negative regions.

The first property is useful to implement closed loop control on an intelligent structure. The second property minimizes the effect of mismodeled or unmodeled higher order dynamics and reduces the effects of aliasing. Aliasing will occur when the wavelength of the mode shape is less than or equal to the length between two successive sensors. The third property avoids possible instabilities in a control scheme using these sensor measurements.

As regards the sensor system as a whole, including the processing of the sensor output to estimate overall shape the following additional objects apply:

4. The sensor system as a whole is such as to resolve the shape of the structure accurately and in detail.

5. Global shape estimates of the structure are to roll off quickly with spatial frequency to avoid aliasing involving static modes of high spatial frequency.

6. The roll off toward zero of the sensor system observability to static modes of increasing spatial frequency is to be monotonic and should not contain any negatives.

This first of these properties is motivated by the fact that the static shape typically contributes significantly to the performance metric in any structural control scheme, because the truncated series of modes used to represent the dynamics of the structure cannot generally be superposed to produce an accurate representation of the static structural shape in order to assure good performance. With sensors of the present invention applicant uses numerical spatial integration in order to estimate the global shape from the individual sensor measurements. The next property assures that the observability of the sensor system to static modes of relatively high spatial frequency will decrease. Aliasing will occur when the wavelength of the static mode is less than or equal to the length between two successive sensors. The last property stems from the fact that negatives appearing in the roll off of the sensor system observability would be capable of instigating unstable interactions in a control scheme using these sensor measurements. Such negatives could be introduced, for example, by sensor aliasing.

Finally as regards the physical implementation of a distributed sensor system:

7. The sensors are to be of finite length, implementable on practical structures.

8. Sensors are not have partially negative or highly complex weightings.

9. Sensors near structure boundaries must be susceptible of truncation in such a way as to not degrade performance.

The finitude property is evident: the required length of the sensor cannot exceed the physical length of the structure. The next property addresses ease of sensor implementation. Ease of implementation is of great concern in order to assure accuracy and the performance predicted analytically. Thus sensors whose weighting is everywhere non-negative are desirable, because fabrication of such sensors is significantly easier than sensors that require regions of negative weighting. In addition sensors of other complex shapes would have to be fabricated very accurately to ensure that they exhibit the properties predicted analytically. The final property requires that sensors that would ordinarily extend beyond a boundary of the structure must be capable of truncation in such fashion that they can be implemented in a practical setting.

Within the scope of the foregoing objects, applicant's invention includes sensors and systems using such sensors, as described below.

In general terms, applicant has found that a sensor useful for generalized sensing and development of control system includes an element mounted on or in proximity to a surface or structural member for sensing a property thereof and producing an output, wherein the sensor extends over a region or patch, and has a weighting or sensitivity that decreases away from its center. In various embodiments, the weight may decrease to zero at edges of and active sensing region, and may decrease as a linear, trigonometric, exponential or other function, symmetrically or asymmetrically toward its edge. For other embodiments higher derivatives of the weight are required to meet specific conditions of continuity or boundedness.

One embodiment especially adapted to placement proximate to an edge of a sensed surface has a weighting which is functionally derived by reflection and inversion of a truncated portion of a full area sensor.

Systems using sensors according to the invention include a plurality of sensor placed over possibly overlapping regions of a structure. Like the individual sensors, the systems have the property that the effect of higher order modes on the sensors falls rapidly toward zero.

Individual sensors preferably sense spatial variables of the structure, such as displacement or slope, or spatial derivatives of a variable, such as strain.

Sensors according to the invention include active portions utilizing any of a number of sensing technologies, such as piezoelectric, resistive, capacitive or radiation sensitive materials, the output sensitivity distribution varying over the active sensing region. The weighting function is achieved in one piezoelectric embodiment, by forming an active metallized or conductive electrode region having an area corresponding in shape to the desired weighting. A resistive sensor may be implemented by fabricating the resistive element with a linear density corresponding to the desired weighting function. Various forms of capacitive sensor may be implemented by introducing variations in discrete electrode area, or in dielectric thickness to achieve similar weightings. Other sensor technologies achieve weighted outputs by similar adjustment of their basic physical structure.

Effective implementation of systems according to the invention requires consideration of the following design parameters: (1) the spatial and temporal derivative sensed; (2) the sensor weighting; (3) the sensor length; (4) the boundary sensor design; (5) the integration method; (6) the number of sensors. The investigation of these parameters in the detailed description, below, will provide a deeper understanding of the invention herein and its differences from the prior art.

The first design parameter that must be considered deals with the spatial variable of the structure which will be measured by the sensors. Possible spatial derivatives of a structure that could be sensed are absolute displacement, slope or relative displacement, or a continuous variable such as strain. The displacement is difficult to measure without time integration of an inertial acceleration or without a reference to a relative frame. Perhaps the easiest spatial derivative to measure, however, is strain, since it is continuous, and is amenable to weighted measurements. True static shape estimation may be performed using sensors which measure some spatial derivative of displacement such as strain, rather than temporal derivatives of displacement such as velocity or acceleration. By using spatially filtering sensors with appropriate weightings, the observability of such sensors will roll off as the spatial frequency of the spatial derivative being measured increases. Sensors that spatially average strain are more easily implemented than ones that average displacement. Thus for proof-of-principal modeling and prototypes, applicant has taken a sensor system composed of spatially averaging strain sensors whose output is spatially integrated using a numerical integration scheme in order to obtain the quasistatic and dynamic states of the structure.

The spatial weighting of the sensor determines the transfer function of the sensor and how its output will be affected by the spatial frequency of the longitudinal strain field that acts on it. The description below deals with the performance and design of individual spatially filtering strain sensors. The design of the weighting function used for the sensors is described, and these weightings are analysed and the effect of the sensor shape on the transfer function and output is derived in detail, for both sinusoidally and exponentially varying strain fields. The effect of moving the sensors along the length of the structure on the sensor output and transfer functions is also addressed.

All spatially filtering sensors of finite length roll off beyond some spatial frequency with at least $-20$ db/decade. The point at which this rolloff begins is defined as the point where the transfer function (the output of the sensor relative to the output of a point sensor at its center) has dropped to ($-3$ dB), and is largely controlled by the effective length of the sensor. As the sensor is lengthened the spatial frequency at which rolloff begins decreases. This is because more wavelengths of a strain field at a fixed spatial frequency can be fitted within the length of a longer sensor, and the spatial frequency of the strain field becomes considerably higher than the weighting of the sensor. The effect of sensor length on the sensor transfer function is also discussed below.

Since the length of the sensors employed is finite, in fabricating a system from plural copies of a single standard sensor, it will be generally impossible to avoid having a sensor which would normally extend beyond a boundary of the structure. The design of such sensors and the method by which the weighting is truncated is very important as it has a significant effect on the performance of the sensors. Attention is therefore also given below to the properties of sensors whose weighting partially falls beyond the boundary of the structure. These properties are derived and analysed, and two methods of truncation for sensors near a structure boundary are presented.

Once the design of the sensors has been established, it is necessary to decide what scheme should be used to estimate the global slope and deflection of the structure using the outputs of the sensor array. The array of strain sensors will yield curvature measurements along the length of the structure, in the case of bending. These curvatures can be numerically integrated twice to estimate the global deflections of the structure. The invention thus also includes integration schemes for determining shape. Representative integration schemes include the simple midpoint, trapezoidal and Simpson rules, and two rules based on cubic interpolating splines and second order B-splines. In addition, two optimal quadrature rules, the Gauss and Radau methods, and a conventional interpolation scheme using Chebyshev polynomials are included, although the invention is not restricted to systems employing these simpler numerical techniques.

One-dimensional structures, such as beams, are described as an example for implementation. The static shape and dynamic modes of such a structure are sensed by a sensor array mounted on the surface, along the length of a beam-like structure. Numerical integration schemes may be used to obtain global shape estimates by numerically integrating the measurements made by the sensor array.

In simulations applicant has assessed the performance of the integration schemes for quasistatic loadings and a varying number of sensors in the array. Uncertainties in the gage factor and sensor position were included in an effort to model the errors typically encountered in a practical implementation, in order to determine when is it more beneficial to improve the accuracy of the individual sensors or increase the number of sensors to achieve the best shape estimation possible. In these simulations, the dynamic modes of both pinned-pinned and clamped-free beams were used to assess the rolloff behavior of the spatial integral of the sensor outputs. Pinned-pinned and clamped-free beams with an array of nine evenly distributed sensors were simulated, and, as the mode number increased, global shape estimation was performed, and the tip deflection found. The observability of the sensor system to the mode shape was computed to verify observability roll off as the mode number increased.

In general, the number of sensors distributed along the structure, in conjunction with the integration rules, was found to be important in achieving the level of estimation accuracy required. The convergence properties of the integration rules are preferably selected to guarantee that as the number of sensors is increased, the integrated result achieves higher accuracy. Optimization is achieved, for example, by performing simulations with different integration rules to derive static shape estimations with simple mechanical structures under different constraints.

BRIEF DESCRIPTION OF THE DRAWINGS

These and other features of the invention will be understood from the description herein, taken together with the drawings, wherein.

DETAILED DESCRIPTION OF THE INVENTION

Applicants hereby incorporate herein by reference their paper "Discrete Shaped Strain Sensors for Intelligent Structures" AIAA Paper 92-2406 presented by them at the 33rd SDM Conference, Dallas Tex., April 13-15, 1992, a copy of which is attached as Appendix A.

In accordance with a basic aspect of the invention, applicant has designed a novel sensor, which unlike a conventional point sensor, s uniform broad area sensor, or a specially shaped or processing sensor, has an unpointlike extent but a non-constant weighting function that is independent of the form or structure being sensed. By independent is meant, simply, that the weighting function is unrelated to mode shape or any specialized processing (e.g., integration, SAW-transform or the like). Instead, applicant's weight function is selected to allow a structure to be covered by a plurality of a single or at most a few types of identical sensors each of which outputs a localized spatially weighted function of the sensed parameter, such that the functions are, individually and globally, well-behaved under spatial transformation.

This allows the design of systems wherein a plurality of discrete, spaced-apart sensors may be located on a structure without knowing the states or properties to be measured, and their outputs combined to form spatial representations valid for the structure as a whole. The implementation of a sensor with this property requires that the sensor's weighting function be decreasing sway from its center, although the precise form of weighting function may differ for different applications, and preferably does differ for sensors which are to be placed near edges of a structure.

Figure 1:
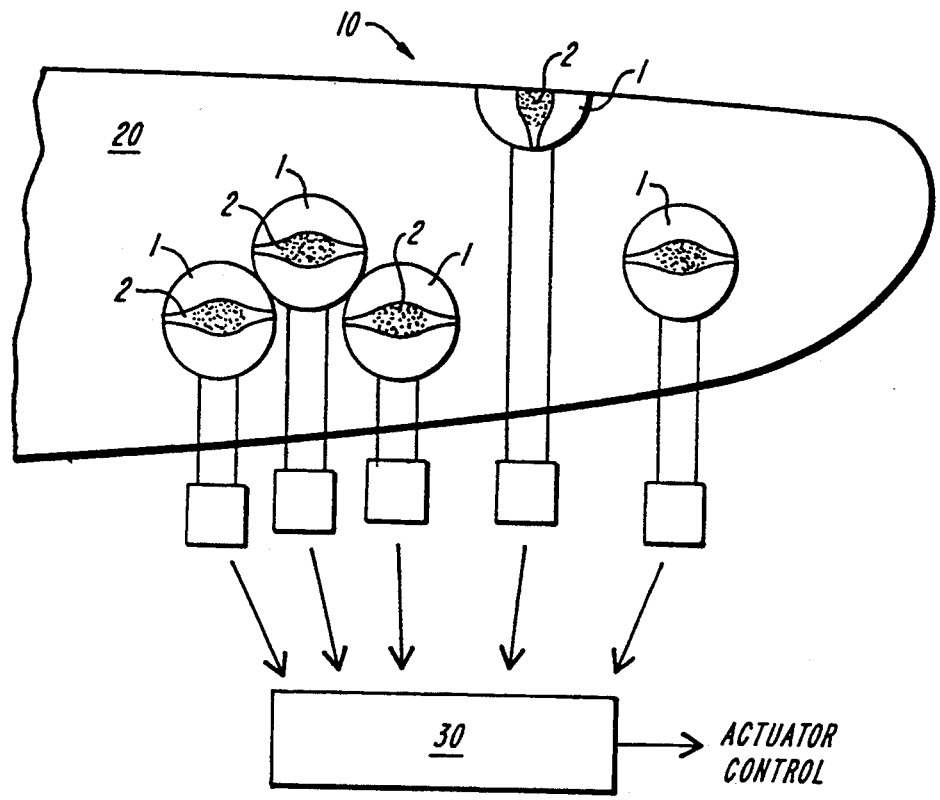
FIG. 1 shows a schematic view of a sensor and system in accordance with the present invention.

FIG. 1 illustrates a system 10 according to the present invention, wherein a structure 30 which represents a wing, hull, sail, aileron, rudder of the like has a major portion of its surface covered by a plurality of possibly overlapping sensors 1 which are connected to a controller 30. Each sensor has an active sensing region, which may coincide with the full extent of the sensor, and a spatial sensitivity or weighting distribution which is indicated generally by the weight shape 2 shown on one sensor.

FIGS. 2A-2E illustrate particular constructions of suitable sensors using diverse sensor technologies.

Figure 2A:
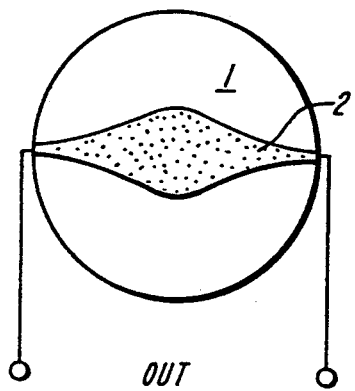
FIGS. 2A-2E show particular sensor embodiments.

As shown in FIG. 2A, a sensor 1 according to the invention may be implemented as a sheet patch of piezoelectric material having an electrode pattern 2 thereon to define an active region, the shape of the electrode defining a weighting function for the patch. As shown, a preferred weighting function tapers continuously to zero near the boundary.

Figure 2B:
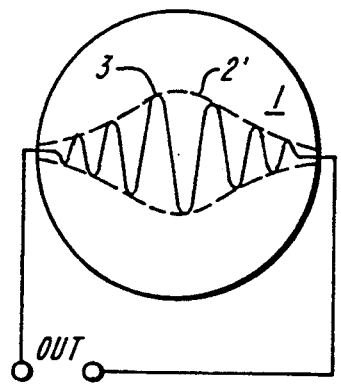

A resistive sensor implementation is shown in FIG. 2B. Here, a resistive wire or line 3 meanders within a shape defined by the weighting envelope 2', such that the linear density of the resistive sensing line 3 at each position along an axis defies the weighting of output sensitivity at that position.

Figure 2C:
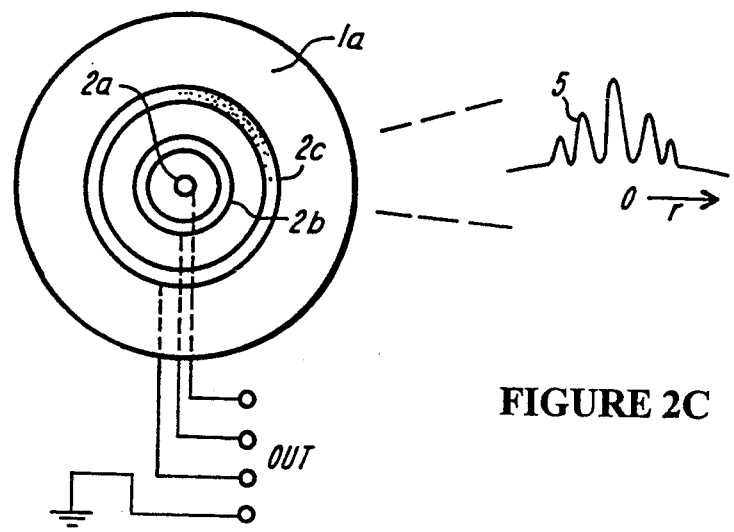

A capacitive sensor is illustrated in FIG. 2C, having an insulative body la supporting a central and one or more annular conductive electrodes $2a$, $2b$, $2c$. The sensor is mounted on or over the surface of a structure, and dielectric material (air or solid film placed between the two), such that the relative areas of the conductors and/or relative thickness of dielectric under each conductor define the weighting 5.

Figure 2E:
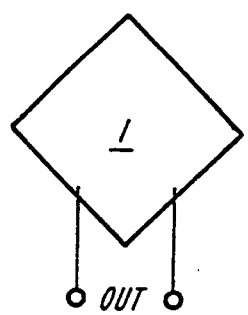
Figure 2D:
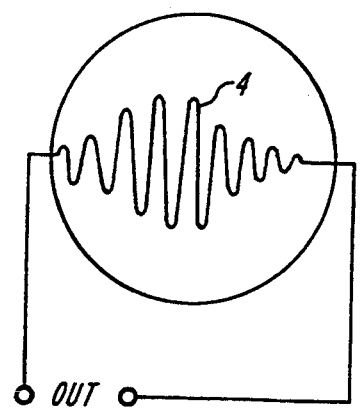

FIG. 2D shows another implementation, similar in geometry to that of FIG. 2B, but characterized by a fiber optic sensing element 4, wherein the fiber is affixed to the structure and receives strain therefrom. This sensor is interrogated by passing light therethrough, the transmission, leakage, back-reflectance or polarization cross-coupling varying in a manner to provide the measurement.

FIG. 2E illustrates a general sensor, it being understood that diverse other sensing technologies such as strain gauge, thin film and others may readily be applied to implement the particular sensor weighting characteristics described below, by doping patterning or the like, to form sensors effective to measure strain, displacement, temperature, or other property of a structure to be controlled.

The weighting to be implemented can be better understood from a careful investigation of weight functions and their suitability to different physical situations. For this purpose, applicant has undertaken an analysis of a number of weighting functions applied to strain field having several common forms, deriving the output and transfer functions for spatially averaging strain sensors applied to strain fields that are spatially sinusoidal, and those that are spatially exponential. Results are obtained for both nontruncated sensors and sensors partially truncated at the boundaries of a structure.

For clarity, basic principles of such spatially averaging sensors are introduced. Then, a set of relatively simple sensor weightings are introduced and defined. General expressions for the output and transfer function of an nontruncated sensor in a spatially sinusoidal strain field are obtained as a function of the parameters that define the spatial weighting of the sensor. Specific results for the chosen weightings are then obtained. Finally, expressions for the output and transfer function of truncated sensors in a sinusoidal strain field are derived, as well as expressions for the output and transfer functions of both nontruncated and truncated sensors in a spatially exponential strain field.

By way of caveat, applicant's spatially averaging sensors can be used in a number of different applications to measure a variety of signals, and need not be limited to measuring spatial variables in structures. For example, applications may be found in acoustics and optics. For the purposes of this description, however, it is assumed that the sensors report measurements of spatially averaged extensional strain signals.

The most important characteristic in the design of spatially averaging strain sensors is their spatial weighting. This weighting determines the way in which the magnitude and phase of the sensor output relative to the strain at the center of the sensor are affected by the spatial variation of the strain field. Let $f(x)$ define the spatial weighting of the sensor. Let this weighting be nonzero over a finite region $[-\frac{l}{2},\frac{l}{2}]$ of the structure. The sensor output is a filtered measurement of the strain of the form $$y = \int_{-l/2}^{l/2} f(x)\epsilon(x)dx \quad (2.1)$$

where $\epsilon(x)$ is the longitudinal strain along the structure and $l$ is the length of the sensor. The weighting function $f(x)$ is implemented by varying the spatial sensitivity of the sensor. Depending on the device used as the sensor, this is done by:

varying the width of the sensor;
varying the thickness of the sensor;
segmenting the sensor and implementing a weighted sum of the measurements of different sensor segments in the signal processing system;
varying the distance of the sensor from the elastic axis of a beam in bending.

Note that the weighting function $f(x)$ is scaled such that $$\int_{-l/2}^{l/2} f(x)dx = 1 \quad (2.2)$$

to assure that strain signals of zero spatial frequency, or infinite spatial wavelength, are measured accurately. This is required in order to satisfy the first design objective discussed above.

As an example of a physical implementation, the sensor may be made of a piece of thin Polyvinylidene Flouride (PVDF) piezoelectric film bonded to the surface of a beam. The weighting function $f(x)$ may be implemented by varying the width of the electrode on the film. The output of the PVDF sensor is a charge proportional to a filtered measurement of the surface strain. Since the magnitude of this charge depends on the area of the electrode, the gain of the sensor can be varied spatially with this technique. The charge generated by the sensor is given by $$Q(t) = d_{31}E_p \int_{-l/2}^{l/2} f(x)\epsilon(x,t)dx \quad (2.3)$$

where $E_p$ is Young's modulus for the piezoelectric film, $f(x)$ is the width of the sensor electrode, $\epsilon(x,t)$ is the surface longitudinal strain, and $d_{31}$ is the piezoelectric constant with units of charge per unit area per unit stress. This constant relates mechanical stress to electric displacement.

This description uses traditional filter theory as a starting point in the design of spatially averaging strain sensors. Classical filter theory has traditionally focused on the processing of sinusoidal or periodic signals in the time domain. This work has led to the design of filters that exhibit a variety of magnitude rolloff and ripple characteristics in the temporal frequency domain. By a transformation from the temporal frequency domain to the spatial frequency domain (the wave number domain), results from classical filter theory can be applied by duality to the design of sensors according to the present invention that provide spatially filtered measurements of strain fields.

Filter theory considers signals in the Fourier domain. Fourier transforms of temporal signals defined in terms of temporal frequency $\omega$ are defined classically as:

$$F(\omega) = \int_{-\infty}^{\infty} f(t)e^{-j\omega t}dt \quad (2.4)$$

Fourier transforms in terms of spatial frequency, $k$ can be developed in a similar fashion:

$$F(k) = \int_{-\infty}^{\infty} f(x)e^{-jkx}dx \quad (2.5)$$

Figure 3A:
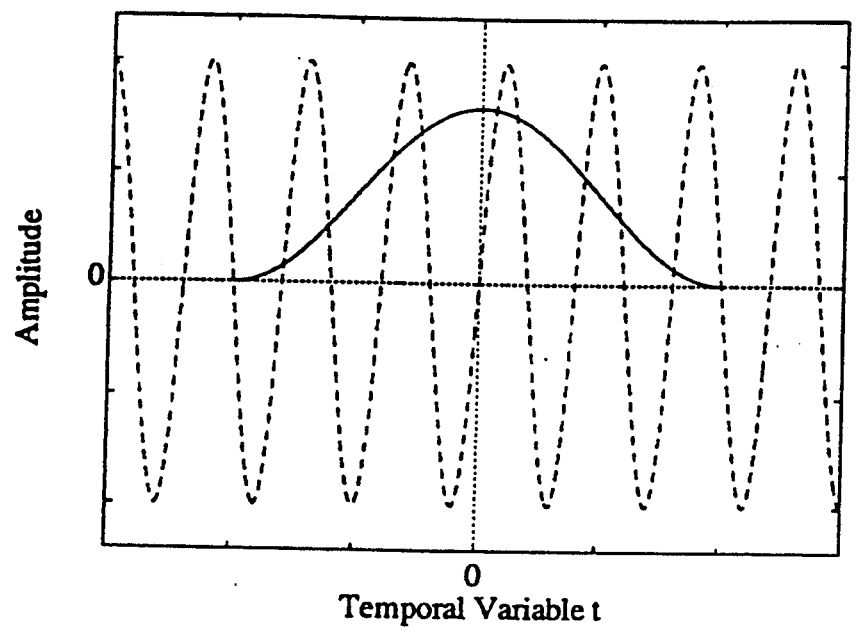
FIGS. 3A and 3B show the correspondence between temporal and spatial system approaches.
Figure 3B:
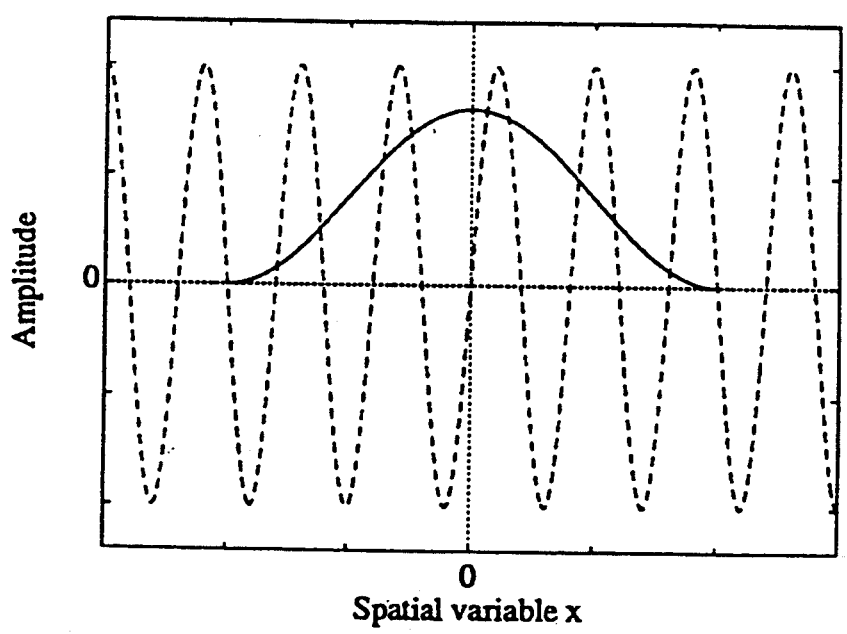

While the spatial frequency $k$ is related to the temporal frequency $\omega$, the spatial sensor weighting acts like a temporal sampling window in time. FIGS. 3A, 3B show this duality clearly. The solid line represents the temporal window $f(t)$ and the spatial weighting $f(x)$, and the dashed line represents the temporal signal $e^{-j\omega t}$ and the spatial signal $e^{-jkx}$.

Due to these similarities, design techniques available for sampling windows can be extended to applications involving spatial filtering. As with temporal windows, the spatial weighting can be changed to tailor the magnitude response, and the effective sensor length can be changed to control the spatial frequency at which magnitude rolloff commences. This rolloff should be quick in order to satisfy the second object required of the sensors as stated above. Note that if $f(x)$ is symmetric about $x=0$, $F(k)$ will be purely real, as the imaginary component drops out. This means that $F(k)$ can exhibit magnitude rolloff without incurring phase lag. However, $F(k)$ can still be negative, indicating a 180° phase shift. The third object stated above states that the individual sensors must have transfer functions that are nonnegative for all values of $k$ in order to avoid possible instabilities in a control scheme using spatially averaging sensors. Such phase uncertainties do exist even in relatively simple situations for certain weightings and must be avoided.

For investigating spatial weightings of sensors, some simple ones which are used in temporal windowing of temporal signals are presented here. Such window shapes include rectangular, Bartlett (or triangular) and Hanning windows. In addition, Sinc and Gaussian sensor weightings are also presented because they possess interesting frequency characteristics. Using these simple shapes, more complicated ones are created by multiplying the weightings of two or more simple weightings together. Examples of these include a Sinc weighting multiplied by another Sinc weighting, a Bartlett weighting multiplied by another Bartlett weighting, a Hanning weighting multiplied by another Hanning weighting, and a Gaussian multiplied by a Hanning weighting. A number of such complex weightings are described in order to demonstrate what spatial properties a weighting should posses to assure that its transfer function will have certain desired properties.

Figure 4:
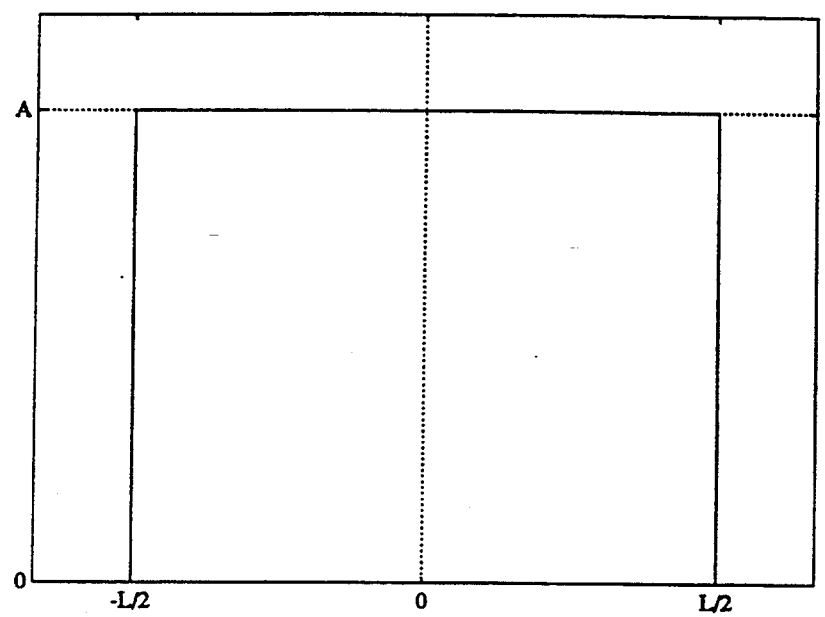
FIGS. 4-6 illustrate three different spatially finite sensor weightings.
Figure 5:
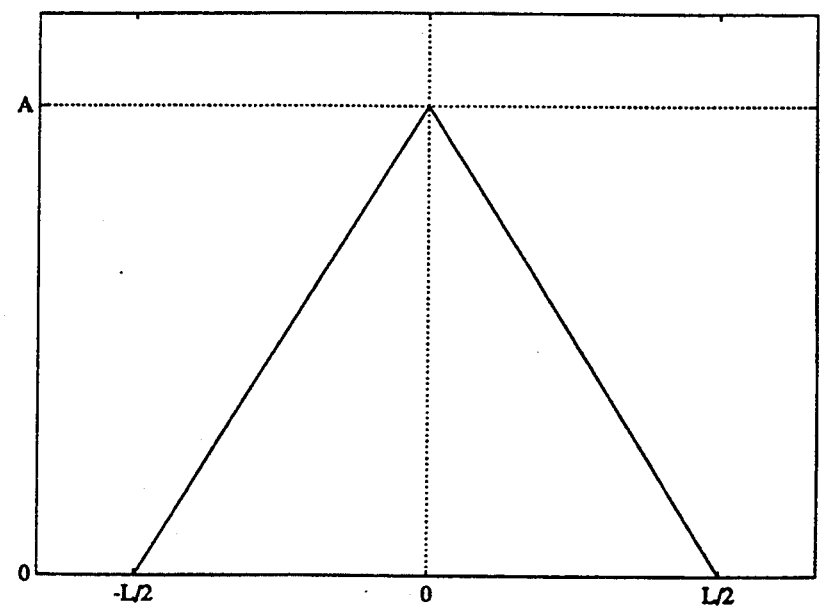
Figure 6:
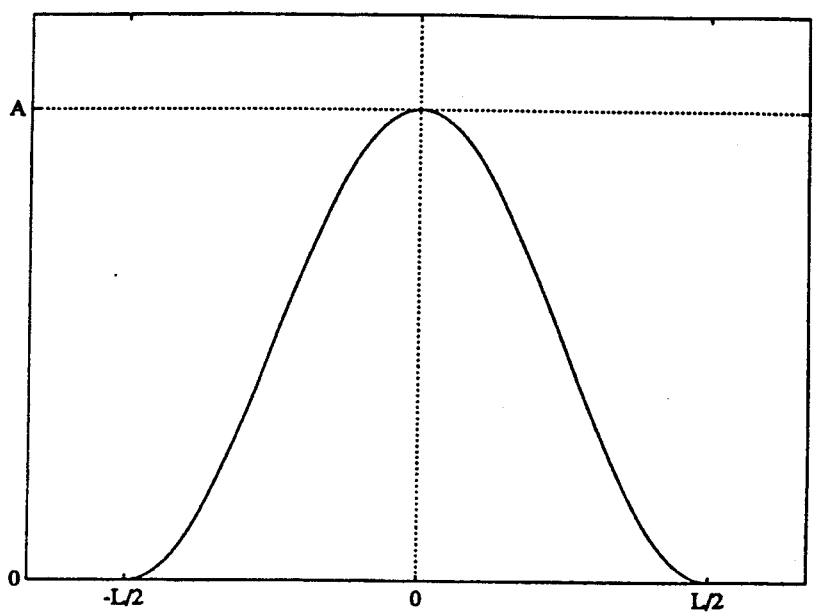
Figure 7:
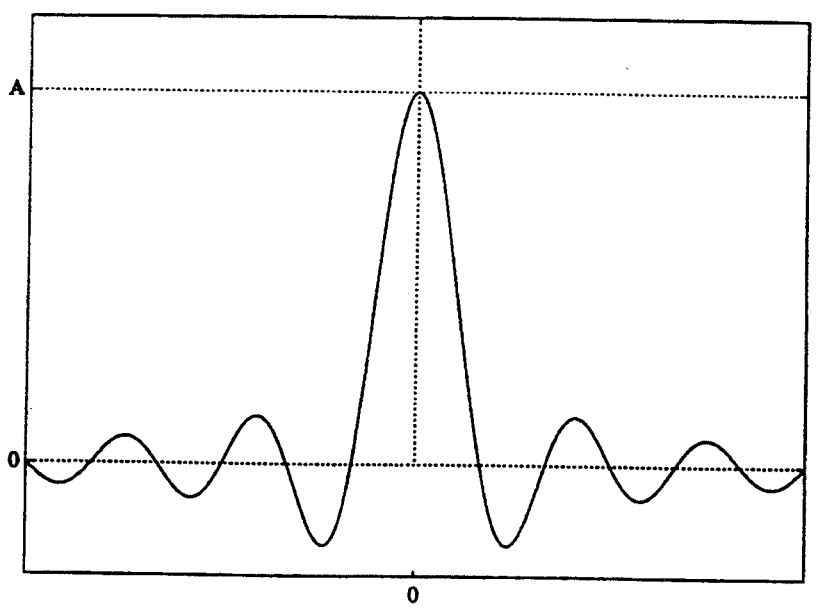
FIGS. 7-9 illustrate three different spatially infinite sensor weightings.
Figure 8:
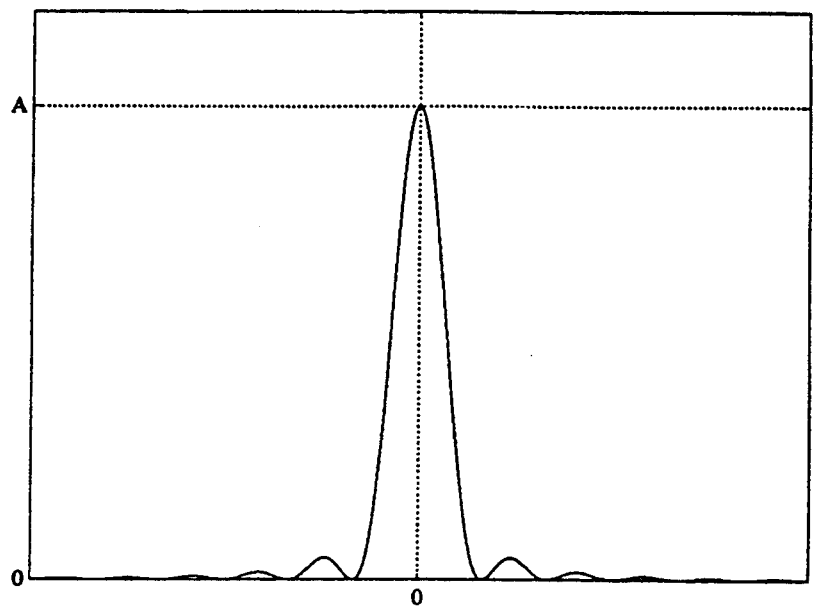
Figure 9:
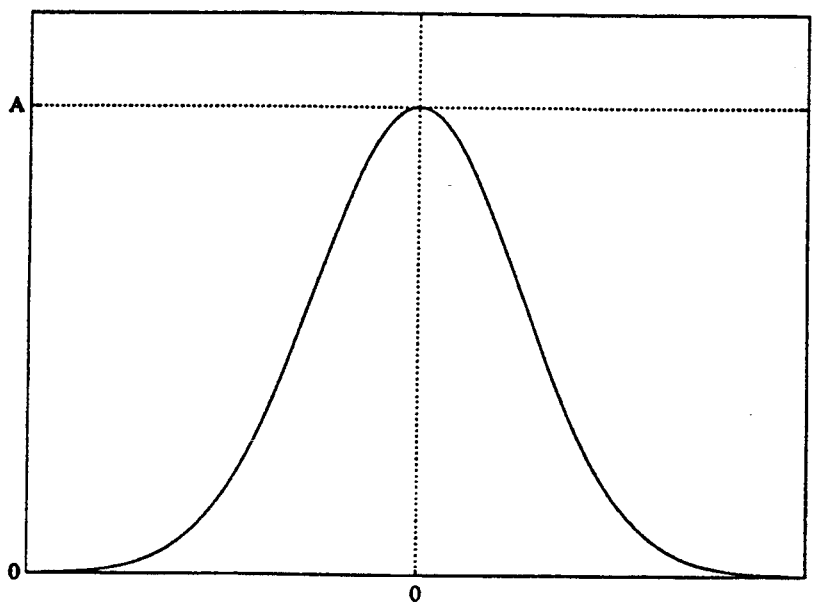
Figure 10:
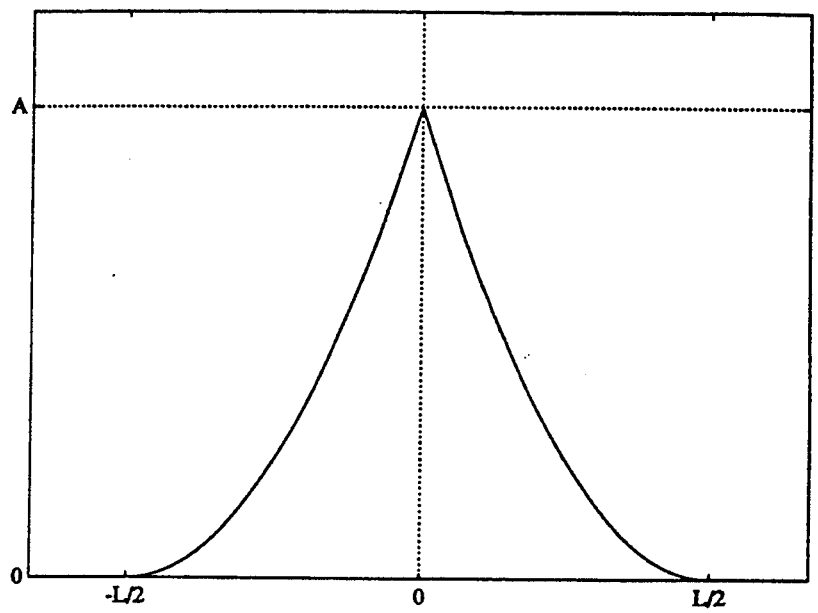
FIGS. 10-12 illustrate different compound weightings.
Figure 11:
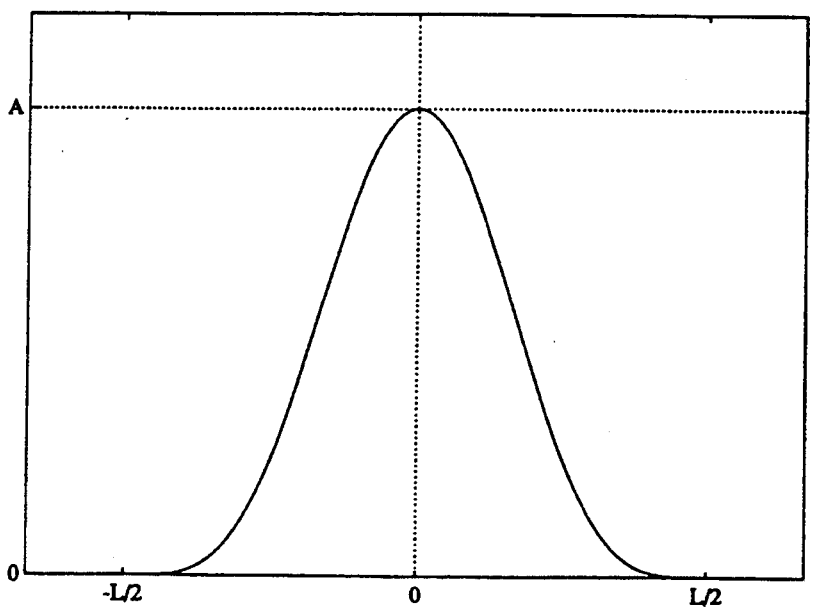
Figure 12:
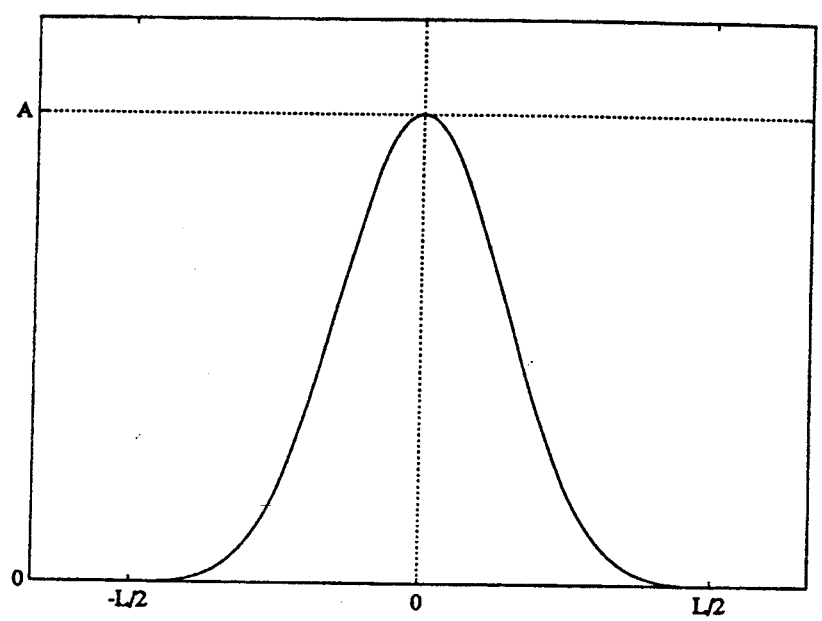

In the following, the sensor weightings are defined. The parameter $\alpha$ is used to select the effective length of the sensor. It will be seen later that this parameter is scaled in such a way that the magnitude response to a sinusoidal field drops to ($-3$ dB) exactly or in the vicinity of $k=\alpha$. In the following three sections the spatial definitions of nine selected sensors will be presented. In FIGS. 4, 5 and 6 definitions of three spatially finite weightings are shown. In FIGS. 7-9 the definitions of three spatially infinite weightings are given. Finally, FIGS. 10-12 show three compound weightings obtained by multiplying two weightings together.

The rectangular, or box car weighting is shown in FIG. 2.2, and is defined as $$f(x) = \frac{\alpha}{2\sqrt{2}}, \quad -\frac{\sqrt{2}}{\alpha} \leq x \leq \frac{\sqrt{2}}{\alpha} \tag{2.6}$$

Note that the magnitude of f(x) has been chosen such that $$\int_{-\sqrt{2}/\alpha}^{\sqrt{2}/\alpha} f(x)dx = 1.$$

The length l and maximum amplitude A of the rectangular weighting are given by $$l = \frac{2\sqrt{2}}{\alpha} \tag{2.7}$$

$$A = \frac{\alpha}{2\sqrt{2}} \tag{2.8}$$

The Bartlett, triangular, or Parzen weighting is shown in FIG. 5, and is defined by $$f(x) = \frac{\alpha}{2}\left(1 - \left|\frac{\alpha x}{2}\right|\right), \quad -\frac{2}{\alpha} \leq x \leq \frac{2}{\alpha} \tag{2.9}$$

The length and maximum amplitude of the Bartlett weighting are $$l = \frac{4}{\alpha} \tag{2.10}$$

$$A = \frac{\alpha}{2} \tag{2.11}$$

The Hanning weighting is defined by $$f(x) = \frac{\alpha}{\sqrt{2}\,\pi}(1 + \cos(\sqrt{2}\,\alpha x)), \quad -\frac{\pi}{\sqrt{2}\,\alpha} \leq x \leq \frac{\pi}{\sqrt{2}\,\alpha} \tag{2.12}$$

and is shown in FIG. 6. The length and maximum amplitude of the Hanning weighting are given by $$l = \frac{\sqrt{2}\,\pi}{\alpha} \tag{2.13}$$

$$A = \frac{\alpha}{2\sqrt{2\pi}} \tag{2.14}$$

The Sinc weighting is defined by $$f(x) = \frac{\alpha}{\pi}\left(\frac{\sin \alpha x}{\alpha x}\right), \quad -\infty < x < +\infty \tag{2.15}$$

and is shown in FIG. 7. The Sinc weighting extends over $[-\infty, +\infty]$, and its maximum amplitude A is given by $$A = \frac{\alpha}{\pi} \tag{2.16}$$

The Sinc-Sinc weighting is produced by multiplying two Sinc functions together. The result is shown in FIG. 8, and is defined by $$f(x) = \frac{\sqrt{2}+1}{\sqrt{2}}\frac{\alpha}{\pi}\left[\frac{\sin\left(\frac{\sqrt{2}+1}{\sqrt{2}}\alpha x\right)}{\frac{\sqrt{2}+1}{\sqrt{2}}\alpha x}\right]^2, \tag{2.17}$$

$$-\infty < x < +\infty$$

As with the Sinc weighting, the Sinc-Sinc weighting extends over $[-\infty, +\infty]$. Its amplitude A is given by $$A = \frac{\sqrt{2}+1}{\sqrt{2}}\frac{\alpha}{\pi} \tag{2.18}$$

The Gauss weighting is defined by $$f(x) = \frac{\alpha}{\sqrt{2\pi \ln 2}}\exp\left(-\frac{(\alpha x)^2}{2\ln 2}\right), \quad -\infty < x < +\infty \tag{2.19}$$

FIG. 9 shows the shape of the Gauss weighting. As with the Sinc weighting, the Gauss weighting extends over $[-\infty, +\infty]$. Its maximum amplitude A is given by $$A = \frac{\alpha}{\sqrt{2\pi \ln 2}} \quad (2.20)$$

The Bartlett-Bartlett weighting is produced by multiplying two Bartlett weightings together. The resultant weighting is shown in FIG. 10. It is defined by $$f(x) = \frac{3\alpha}{2\pi} \left(1 - \left|\frac{\alpha x}{\pi}\right|\right)^2, \quad -\frac{\pi}{\alpha} \leq x \leq \frac{\pi}{\alpha} \quad (2.21)$$

The length and maximum value of the Bartlett-Bartlett weighting are $$l = \frac{2\pi}{\alpha} \quad (2.22)$$

$$A = \frac{3\alpha}{2\pi} \quad (2.23)$$

The Hanning-Hanning weighting is constructed by multiplying two Hanning weightings together. The result is a weighting that tapers to zero more smoothly than a pure Hanning weighting. The weighting is defined by $$f(x) = \frac{\alpha}{3\pi} (1 + \cos \alpha x)^2, \quad -\frac{\pi}{\alpha} \leq x \leq \frac{\pi}{\alpha} \quad (2.24)$$

The Hanning-Hanning weighting is shown in FIG. 11. The length and maximum amplitude of the Hanning-Hanning weighting are given by $$l = \frac{2\pi}{\alpha} \quad (2.25)$$

$$A = \frac{\alpha}{6\pi} \quad (2.26)$$

The Gauss-Hanning weighting is produced by truncating a Gaussian weighting by multiplying it by a Hanning weighting. The Gauss-Hanning weighting is defined by $$f(x) = M(\alpha)\exp\left(-\frac{(\alpha x)^2}{2\ln 2}\right)[1 + \cos(\sqrt{2}\,\alpha x)], \quad (2.27)$$

$$-\frac{\pi}{\sqrt{2}\,\alpha} \leq x \leq \frac{\pi}{\sqrt{2}\,\alpha}$$

and is shown in FIG. 12 The amplitude parameter $M(\alpha)$ is found by requiring $$\int_{-l/2}^{l/2} f(x)dx = 1.$$

It is given by $$M(\alpha) = \frac{4\alpha}{\sqrt{2\pi \ln 2}} \left[ \frac{1}{erf\left(\frac{\pi + j2\ln 2}{2\ln 2}\right) - erf\left(\frac{-\pi + j2\ln 2}{2\ln 2}\right) + 4erf\left(\frac{\pi}{2\sqrt{\ln 2}}\right)} \right] \quad (2.28)$$

$$M(\alpha) \approx \frac{0.68985}{\sqrt{2\pi \ln 2}} \alpha \approx 0.33056\alpha \quad (2.29)$$

where $j = \sqrt{-1}$, and $erf(z)$ is the error function given by $$erf(z) = \frac{2}{\sqrt{\pi}} \int_0^z e^{-t^2} dt \quad (2.30)$$

The length and maximum amplitude of the Gauss-Hanning weighting are given by $$l = \frac{\sqrt{2}\,\pi}{\alpha} \quad (2.31)$$

$$A = \frac{M(\alpha)}{2} \quad (2.32)$$

Table I summarizes some of the spatial properties of the set of weightings shown in FIGS. 4–12. The second column shows which of the sensor weighting functions contain some negative regions. Of the weightings selected, only the Sinc sensor contains regions of negative sensitivity. The third column of the table specifies whether or not the weighting is spatially finite. It is interesting to note that the Sinc, Gauss and Sinc-Sinc weightings, which will be shown below to offer the best performance, are not spatially finite. The last column of Table I shows the total length of the sensor.

TABLE I

Spatial properties of selected strain-averaging sensors.

| Sensor Type | Sensor Weighting | Negatives in x? | Finite in x? | Length l |
|---|---|---|---|---|
| Finite | Rectangle | No | Yes | $2\sqrt{2}/\alpha$ |
|  | Bartlett | No | Yes | $4/\alpha$ |
|  | Hanning | No | Yes | $\sqrt{2\pi}/\alpha$ |
| Infinite | Sinc | Yes | No | ∞ |
|  | Sinc-Sinc | No | No | ∞ |
|  | Gauss | No | No | ∞ |
| Compound | Bartlett-Bartlett | No | Yes | $2\pi/\alpha$ |
|  | Hanning-Hanning | No | Yes | $2\pi/\alpha$ |
|  | Gauss-Hanning | No | Yes | $\sqrt{2\pi}/\alpha$ |

The results in Table I can now be compared to the objects of the invention stated above. The third column of Table I shows that only the Sinc weighting must contain negative regions. As noted above such negative regions should be avoided as they complicate the sensor fabrication process.

It is necessary for this invention that the weighting be finite in x so as to be implementable in a physical system. Thus, all the spatially infinite weightings (Sinc, Sinc-Sinc and Gauss) cannot be used in sensors according to the invention without some sort of spatial truncation. Preferably this truncation is done in such a way so as not to degrade sensor performance. One such truncation method is given by the compound Gauss-Hanning weighting, where the infinite Gauss weighting is smoothly truncated by multiplication with a finite Hanning weighting.

In the following discussion, the output and transfer functions for spatially averaging strain sensors are derived for both a sinusoidally and an exponentially varying strain field.

At this point, the properties of the weightings of sensors measuring spatially sinusoidal strain signals are described. The placement of sensors relative to the point of symmetry in the strain field is important. This point of symmetry or antisymmetry is defined as the point about which a sinusoidal strain signal remains an odd function and a cosinusoidal strain signal remains an even function, no matter how the spatial frequency is changed. For example, for the strain fields sin(kx) and cos(kx), the point of antisymmetry and symmetry, respectively, is simply $x=0$. This point has the additional property that the strain remains independent of the spatial frequency k.

We first describe the properties of a sensor whose center is positioned at the point of symmetry of the strain field, then, the sensor is moved and the properties of a sensor placed with its center at a known distance $x_o$ from the point of symmetry are found. Since some sensors will inevitably be placed close enough to a boundary of the structure that a portion of their weighting falls beyond it, in this case the weighting is truncated at the boundary. The properties of a truncated sensor are investigated later. Finally an alternative truncation scheme (folded truncation) is introduced and its properties are analysed.

Since a spatially averaging sensor acts as a spatial filter, it is important to investigate the properties of its output and transfer function. The transfer function is defined as the ratio of the filtered strain measurement the sensor reports, to the strain at the center of the sensor. For a spatially constant strain field, the transfer function would be unity allowing a small sensor to be used much like a conventional point sensor. In the following discussion it is assumed that the center of the sensor lies at the point of symmetry in the strain field. Assuming that the weighting function f(x) is non-zero only over the closed interval $[-\frac{1}{2},\frac{1}{2}]$, its output as a function of the spatial frequency k of the strain field is $$y(k) = \int_{-l/2}^{l/2} f(x)\epsilon(k,x)dx \quad (2.33)$$

where $\epsilon(k,x)$ is the extensional strain along the structure as a function of the spatial variable x and the wave number k. Since $\epsilon(k,0)$ is the strain at the center of the sensor, the transfer function of the sensor can be found from $$T(k) = \frac{y(k)}{\epsilon(k,0)} = \frac{\int_{-l/2}^{l/2} f(x)\epsilon(k,x)dx}{\epsilon(k,0)} \quad (2.34)$$

For the case of cosinusoidal strain, where $\epsilon(k,x)=\cos(kx)$, this expression simplifies to $$y(k) = T(k) = \int_{-l/2}^{l/2} f(x)\epsilon(k,x)dx \quad (2.35)$$

since $\cos(0)=1$.

The strain field has been assumed to be of the form $\cos(kx)$ and not $\sin(kx)$ to avoid a zero strain condition at the center of the sensor. It will be shown below that when f(x) is symmetric (that is, when $f(x)=f(-x)$), the transfer function is the same for both sinusoidal and cosinusoidal strain fields. This means that their sine and cosine transforms are identical.

When f(x) is symmetric, the transfer function (2.35) is also the spatial Fourier transform of the weighting function f(x). The spatial Fourier transform of the spatial weighting f(x) is defined as $$F(k) = \int_{-\infty}^{\infty} f(x)e^{-jkx}dx \quad (2.36)$$

Since f(x) is nonzero only over $[-\frac{1}{2},\frac{1}{2}]$, we have $$F(k) = \int_{-l/2}^{l/2} f(x)e^{-jkx}dx \quad (2.37)$$

Expanding the complex exponential $e^{-jkx}$ yields $$F(k) = \int_{-l/2}^{l/2} f(x)\cos(kx)dx - j\int_{-l/2}^{l/2} f(x)\sin(kx)dx \quad (2.38)$$

Since f(x) has been assumed to be symmetric, it is an even function. The product $f(x)\sin(kx)$ is therefore odd, since $\sin(kx)$ is odd. The second integral in (2.38) is therefore zero. Equation (2.38) then equals (2.35):

$$F(k) = \int_{-l/2}^{l/2} f(x)\cos(kx)dx = T(k) = y(k) \quad (2.39)$$

By integrating Equation (2.39) by parts repeatedly, an infinite series solution for the output of a sensor mounted in the interior of the structure, away from its boundaries, centered at the point of symmetry in a cosinusoidal strain field can be written as $$y(k) = T(k) = \sum_{i=0}^{\infty} \left\{ \frac{(-1)^i}{k^{2i+1}} [f^{(2i)}(l/2) + f^{(2i)}(-l/2)]\sin(kl/2) + \frac{(-1)^i}{k^{2i+2}} [f^{(2i+1)}(l/2) - f^{(2i+1)}(-l/2)]\cos(kl/2) \right\} \quad (2.40)$$

where f(i)(x) represents the i-th derivative of the weighting function f(x) with respect to the spatial variable x, $d^i f(x)/dx^i$. The derivation of (2.40) assumes that f(x) has a continuous derivative and is integrable over the interval $[-\frac{1}{2},\frac{1}{2}]$.

Typically, the weighting function f(x) is symmetric. In this case, we have $$f^{(2i)}(x)=f^{(2i)}(-x) \ (i=0,1,\ldots,\infty) \quad (2.41)$$

$$f^{(2i+1)}(x)=f^{(2i+1)}(-x) \ (i=0,1,\ldots,\infty) \quad (2.42)$$

and (2.40) simplifies to $$y(k) = T(k) = \sum_{i=0}^{\infty} \left\{ \frac{2(-1)^i}{k^{2i+1}} f^{(2i)}(l/2)\sin(kl/2) + \frac{2(-1)^i}{k^{2i+2}} f^{(2i+1)}(l/2)\cos(kl/2) \right\} \quad (2.43)$$

This result shows that the transfer function for a weighting function with derivative continuity depends only on the value of the weighting function and its derivatives at the two ends of the sensor modulated by a sine or cosine function. As higher derivatives are considered, the contributions of the weighting function and its derivatives decreases faster as a function of k. As the weighting function f(x) is tapered more smoothly towards zero at the ends, $f^{(i)}(\pm\frac{1}{2})=0$ for higher and higher values of i, and rolloff rate increases. Table II summarizes this behavior, which is critical to achieving a sensor in which observability of dynamic modes rolls off quickly in frequency.

TABLE II

Summary of rolloff properties of the sensor transfer function T(k) for f(x) with a continuous derivative.

| $f^{(i)}(\pm 1/2)$ | Rolloff | | Comments |
|---|---|---|---|
| $f(\pm 1/2) \neq 0$ | 1/k | −20 dB/decade | Weighting function nonzero at either end. |
| $f(\pm 1/2) = 0$ | $1/k^2$ | −40 dB/decade | Weighting function zero at both ends. |
| $f(\pm 1/2) = 0$ $f'(\pm 1/2) = 0$ | $1/k^3$ | −60 dB/decade | Weighting function and slope zero at both ends. |
| $f(\pm 1/2) = 0$ $f'(\pm 1/2) = 0$ $f''(\pm 1/2) = 0$ | $1/k^4$ | −80 dB/decade | Weighting function, slope and curvature zero at both ends. |

When the weighting is nonzero at either or both ends, as for the rectangular weighting, only 1/k roll off is possible. When the weighting goes to zero at both ends, as for the Bartlett weighting, $1/k^2$ roll off is possible. When the weighting and its slope go to zero at both ends, as for the Hanning weighting, $1/k^3$ roll off is possible. The roll off increases as more and more derivatives of the weighting are made zero at the ends.

Since the weighting function f(x) must have a continuous derivative for (2.40) and Table II to be valid, the Bartlett (triangular) and Bartlett-Bartlett weightings must be considered differently. For a weighting function with a derivative discontinuity at x=0, for example, the integral (2.35) must be written $$y(k) = T(k) = \int_{-l/2}^{0^-} f(x)\cos(kx)dx + \int_{0^+}^{l/2} f(x)\cos(kw)dx \quad (2.44)$$

Equation (2.40) is modified, and the result is $$y(k) = \quad (2.45)$$

$$T(k) = \sum_{i=0}^{\infty} \left\{ \frac{(-1)^i}{k^{2i+1}} [f^{(2i)}(-l/2) + f^{(2i)}(-l/2)]\sin(kl/2) + \frac{(-1)^i}{k^{2i+1}} [f^{(2i+1)}(0^-) - f^{(2i+1)}(0^+) + [-f^{(2i+1)}(-l/2) + f^{(2i+1)}(l/2)]\cos(kl/2) \right\}$$

where $x=0^-$ is a point just before the discontinuity, and $x=0^+$ is a point just after the discontinuity.

Assuming that f(x) is symmetric, and Equations (2.41) and (2.42) apply, (2.45) simplifies to $$y(k) = T(k) = \sum_{i=0}^{\infty} \left\{ \frac{2(-1)^i}{k^{2i+1}} [f^{(2i)}(l/2)\sin(kl/2)] + \frac{2(-1)^i}{k^{2i+2}} [-f^{(2i+1)}(0^+) + f^{(2i+1)}(l/2)]\cos(kl/2) \right\} \quad (2.46)$$

Note the appearance of an extra term proportional to the value of the odd derivatives of f(x) at the point of derivative discontinuity.

Table III summarizes the roll off behavior of sensors with weightings containing a derivative discontinuity. Again, 1/k roll off is assured for any weighting function f(x). To obtain $1/k^2$ rolloff, we must have $f(\pm 1/2)=0$, as for a weighting with no derivative discontinuity. However, to achieve $1/k^3$ rolloff, we need not only $f(\pm 1/2)=0$ and $f'(\pm 1/2)=0$, but also $f'(0^\pm)=0$. That is, the slope of f(x) at the point of higher derivative discontinuity must be zero. since this requirement can only be satisfied when f(x) has no first derivative (slope) discontinuity, it is clear than no more than $1/k^2$ rolloff is obtainable for such weightings. In general, then, for weightings with a discontinuity in the i-th derivative, only $1/k^{i+1}$ rolloff is possible.

TABLE III

Summary of roll off properties of sensor transfer function. T(k) for f(x) with a derivative discontinuity

| $f^{(i)}(\pm 1/2)$ | Rolloff | | Comments |
|---|---|---|---|
| $f(\pm 1/2) \neq 0$ | 1/k | −20 dB/decade | Weighting function nonzero at either end. |
| $f(\pm 1/2 = 0$ | $1/k^2$ | −40 dB/decade | Weighting function zero both ends. |
| $f'(\pm 1/2) = 0$ $f'(0^\pm) = 0$ | $1/k^3$ | −60 dB/decade | Weighting function zero at both ends and slope zero at discontinuity and both ends. |
| $f(\pm 1/2) = 0$ $f'(0^\pm) = 0$ $f''(\pm 1/2) = 0$ | $1/k^4$ | −80 dB/decade | Weighting function and curvature zero at both ends and slope zero at discontinuity and both ends. |

TABLE IV

Frequency properties of selected strain-averaging sensors.

| Sensor type | Sensor Weighting | | Predicted rolloff |
|---|---|---|---|
| Finite | Rectangle | 1/k | −20 dB/Decade |
| | Bartlett | $1/k^2$ | −40 dB/Decade |
| | Hanning | $1/k^3$ | −60 dB/Decade |
| Infinite | Sinc | $1/k^\infty$ | −∞ dB/Decade |
| | Sinc-Sinc | $1/k^\infty$ | −∞ dB/Decade |
| | Gauss | $1/k^\infty$ | −∞ dB/Decade |
| Compound | Bartlett-Bartlett | $1/k^2$ | −40 dB/Decade |
| | Hanning-Hanning | $1/k^5$ | −100 dB/Decade |
| | Gauss-Hanning | $1/k^3$ | −60 dB/Decade |

At this point the properties of transfer functions of the weightings in a spatially cosinusoidal strain field can be investigated in more detail. Table IV shows the predicted rolloff rates of the selected weighting functions introduced earlier. The rectangular weighting has $f(\pm\frac{1}{2})=0$, and should therefore have $1/k$ rolloff by Table II. The Bartlett window has $f(\pm 1/2)=0$ but also a slope discontinuity at $x=0$, and should therefore have $1/k^2$ rolloff by Table II. The Hanning window tapers smoothly to zero and has $f'(\pm\frac{1}{2})=0$. This means it should have $1/k^3$ rolloff. All the derivatives of the infinite windows approach zero at $\pm\infty$, which suggests that their rolloff rate should be $1/k^\infty$ far above the rolloff frequency. For the compound weightings, the Bartlett-Bartlett weighting has a slope discontinuity at $x=0$, and should therefore have $1/k^2$ rolloff. For the Hanning-Hanning weighting, all derivatives up to and including the third are zero. This suggests a rolloff rate of $1/k^5$. The Gauss-Hanning weighting simply tapers to zero as a Hanning weighting, and should therefore have the same rolloff rate, $1/k^3$.

Analytic expressions for the transfer functions of the weightings presented in Table IV will now be derived and discussed in more detail.

The simplest weighting function is the rectangular weighting. It simply averages a signal evenly over a certain domain. The transfer function for the rectangular sensor is a Sinc function. The transfer function is easily derived from (2.40). From a mathematical viewpoint, the weighting function f(x) is nonzero at the endpoints $(x=\pm\frac{1}{2})$, but all the higher derivatives of the rectangular weighting are zero at the ends of the sensor. Thus only a single term remains from the infinite series in (2.40):

$$F(k) = \frac{1}{k}[f(-l/2) + f(l/2)]\sin\frac{kl}{2} \quad (2.47)$$

For the rectangular weighting, $f(-\frac{1}{2})=f(\frac{1}{2})=\alpha/2\sqrt{2}$ and $1/2=l/2/\alpha$ as shown in Equations (2.7) and (2.8). The transfer function then becomes $$T(k) = \frac{1}{k}\left[\frac{\alpha}{2\sqrt{2}} + \frac{\alpha}{2\sqrt{2}}\right]\sin\frac{\sqrt{2}\,k}{\alpha} \quad (2.48)$$

$$T(k) = \frac{\alpha}{\sqrt{2}\,k}\sin\frac{\sqrt{2}\,k}{\alpha} \quad (2.49)$$

Using $\bar{k}=k/\alpha$, we find $$T(k) = \frac{\sin(\sqrt{2}\bar{k})}{\sqrt{2}\bar{k}} \quad (2.50)$$

Figure 13B:
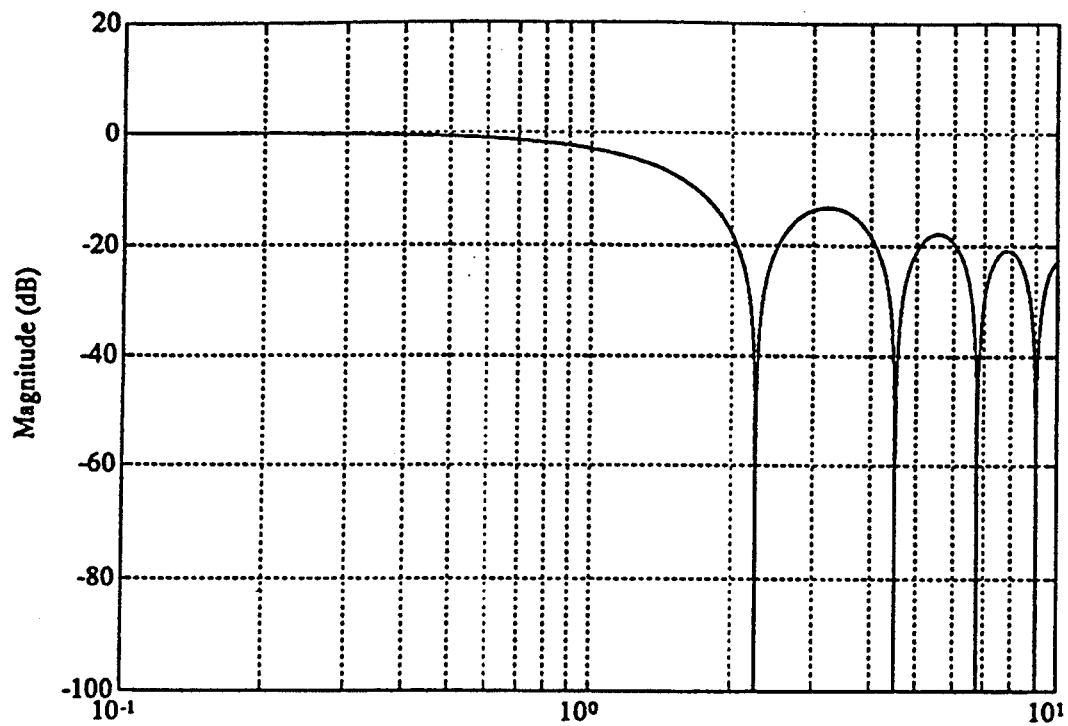
FIGS. 13-15 illustrate transfer functions and phase for the sensor weightings of FIGS. 4-6.
Figure 13B:
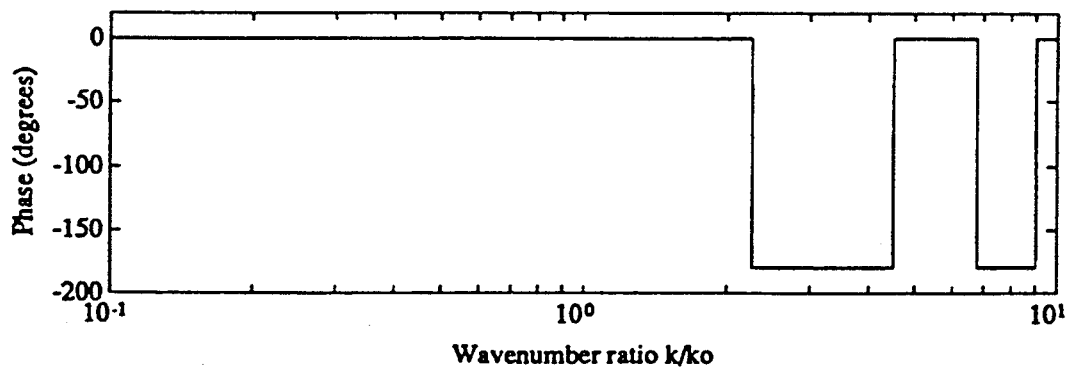

FIG. 13 shows the transfer function and phase for the rectangular weighting. The transfer function begins to roll off for k slightly less than unity. The rolloff point is defined as the point where the magnitude of the transfer function goes below about $-3$ dB. Note that due to the logarithmic scales employed, it is unclear from figure that the transfer function is indeed a Sinc function. Equation (2.50) and Table IV show that the rolloff rate of the rectangular weighting must be $1/k$, or $-20$ db/decade, as shown in FIG. 13. From the phase plot, it is clear that there are sign reversals at each zero of the transfer function shown in (2.50). The first side lobe of the transfer function has a height of $-13.26$ dB.

The Bartlett weighting is used to provide better side lobe response than the rectangular weighting. This weighting can be expressed as a convolution of two rectangular weightings of half the width of the Bartlett weighting.

The transfer function for the Bartlett or triangular weighting is the square of a Sinc function. The transfer function can be derived from (2.45) which takes into account the fact that the Bartlett weighting does not possess first derivative (slope) continuity over the interval $[-\frac{1}{2},\frac{1}{2}]$. Only f(x) and f'(x) are nonzero for the Bartlett weighting. Thus only two terms in the infinite series of (2.45) remain, and we obtain:

$$T(k) = \frac{1}{k}[f(-l/2)\sin(kl/2)] + \frac{1}{k^2}[-f'(-l/2)\cos(kl/2) + \quad (2.51)$$

$$f'(0^-)] + \frac{1}{k}[f(l/2)\sin(kl/2)] + \frac{1}{k^2}[-f'(0^+) + f'(l/2)\cos(kl/2)]$$

$$T(k) = \frac{1}{k}[f(-l/2) + f(l/2)]\sin(kl/2) + \quad (2.52)$$

$$\frac{1}{k^2}[f'(0^-) - f'(0^+) + [-f'(-l/2) + f'(l/2)]\cos(kl/2)]$$

For the Bartlett weighting, $f(-\frac{1}{2})=f(\frac{1}{2})=0$, $f'(-\frac{1}{2})=f(0-)=\alpha^2/4$, and $f'(\frac{1}{2})=f(0+)=-\alpha^2/4$ as shown in (2.9). In addition, $1/2=2/\alpha$, from (2.10).

Thus (2.52) simplifies to $$T(k) = \frac{1}{k^2}\left(\frac{\alpha^2}{4} + \frac{\alpha^2}{4} + \left(-\frac{\alpha^2}{4} - \frac{\alpha^2}{4}\right)\cos\frac{2k}{\alpha}\right) \quad (2.53)$$

$$T(k) = \frac{\alpha^2}{k^2}\left(\frac{1}{2} - \frac{1}{2}\cos\frac{2k}{\alpha}\right) \quad (2.54)$$

$$T(k) = \frac{1}{\bar{k}^2}\left(\frac{1-\cos 2\bar{k}}{2}\right) \quad (2.55)$$

using $\bar{k}=k/\alpha$. Further, using the fact that $1-\cos 2\theta=2\sin^2\theta$, the transfer function (2.55) simplifies to $$T(k) = \frac{\sin^2\bar{k}}{\bar{k}^2} \quad (2.56)$$

Figure 14A:
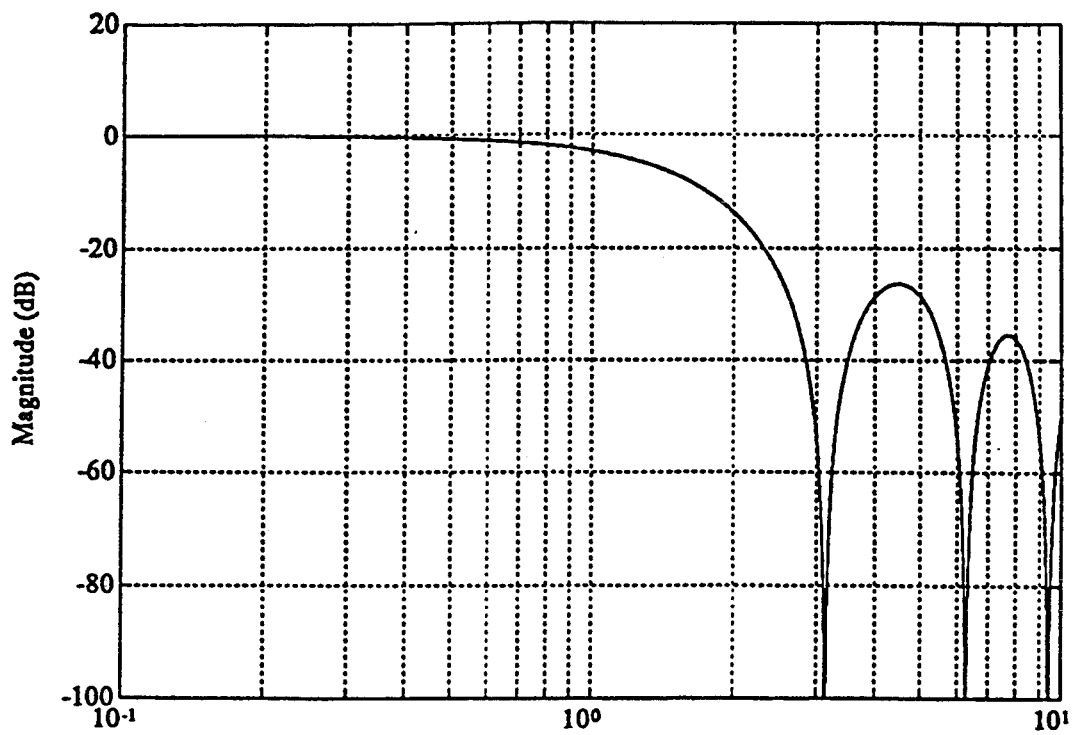
Figure 14B:
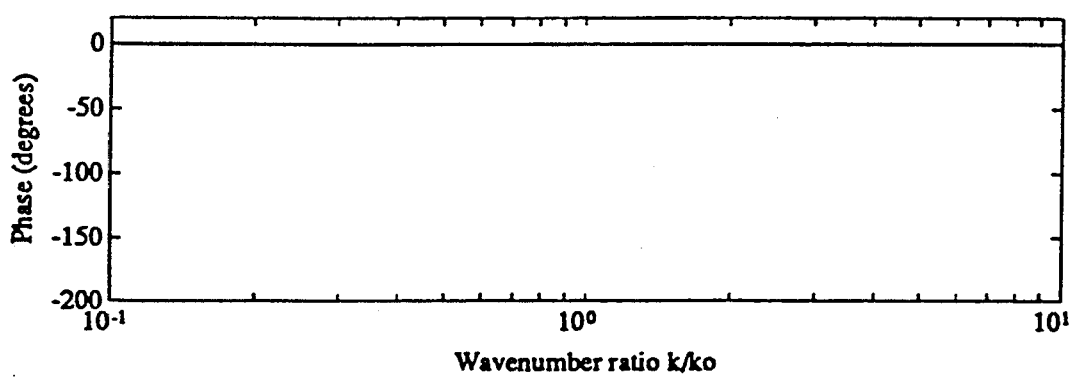

FIG. 14 shows plots of the magnitude and phase of the transfer function for the Bartlett sensor. In Table IV it was predicted that the rolloff of the Bartlett weighting should be $1/k^2$. From FIG. 4 and (2.56) it is clear that this is indeed the case. In addition, the transfer function is non-negative for all values of k, which indicates that the rolloff shown in FIG. 14 is not accompanied by any phase flips of $\pm 180°$.

A convolution in the spatial domain corresponds to a multiplication in the spatial frequency domain. Thus since the Bartlett weighting is the convolution of two rectangular weightings, the transfer function of the Bartlett window is the square of the transfer function of the rectangular weighting. As can be seen from FIG. 14, the side lobes of the transfer function for the Bartlett weighting have been attenuated significantly compared to those for the transfer function of the rectangular weighting. The first side lobe is at −26.52 dB, exactly two times lower than for the rectangular weighting.

The side lobes of the Bartlett weighting can be attenuated further by using the principle of superposition. The result is the Hanning window. Its transfer function is $$T(k) = \frac{1}{2} \frac{\sin(\pi(\bar{k}/\sqrt{2} + 1))}{\pi(\bar{k}/\sqrt{2} + 1)} + \tag{2.57}$$

$$\frac{1}{2} \frac{\sin(\pi(\bar{k}/\sqrt{2} - 1))}{\pi(\bar{k}/\sqrt{2} - 1)} + \frac{\sin(\pi\bar{k}/\sqrt{2})}{\pi\bar{k}/\sqrt{2}}$$

Figure 15A:
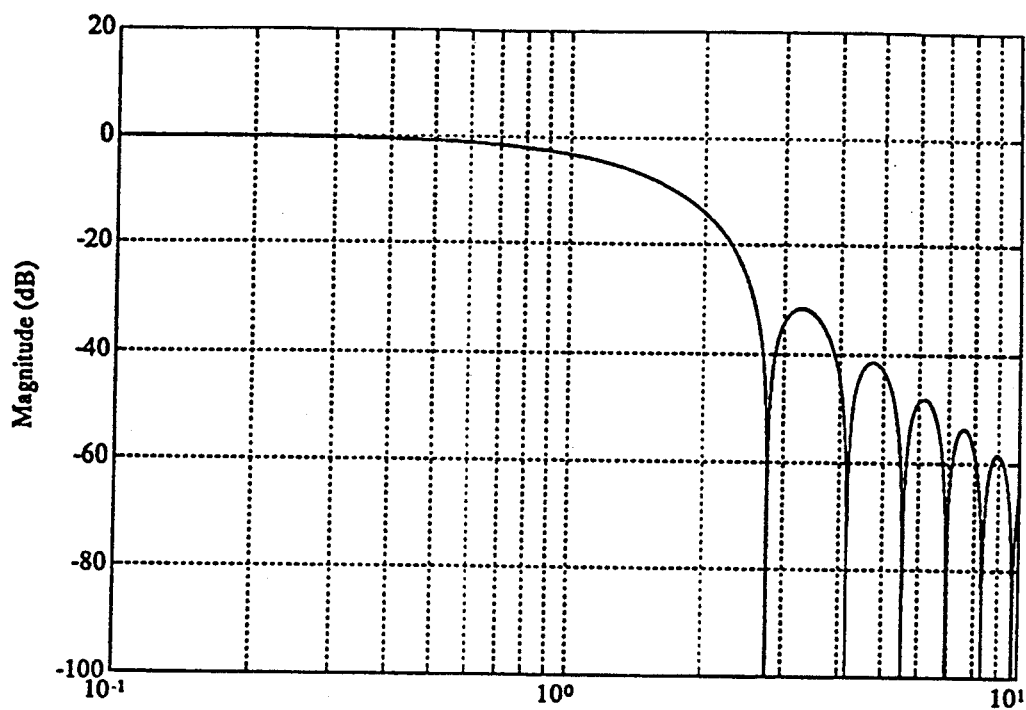
Figure 15B:
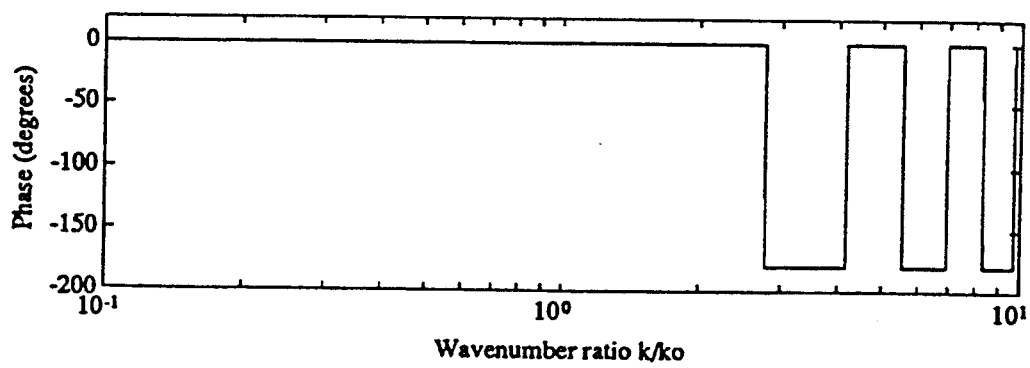

FIG. 15 shows the magnitude and phase of the transfer function for the Hanning weighting. The Hanning weighting yields a rolloff rate of −60 dB/decade, as predicted in Table IV, an improvement of −20 dB/decade over the Bartlett weighting. However, from the phase plot in FIG. 15 it can be seen that there are now phase reversals at every zero of the transfer function. The first side lobe has a height of −31.47 dB, a fair improvement over the Bartlett weighting.

Figure 16A:
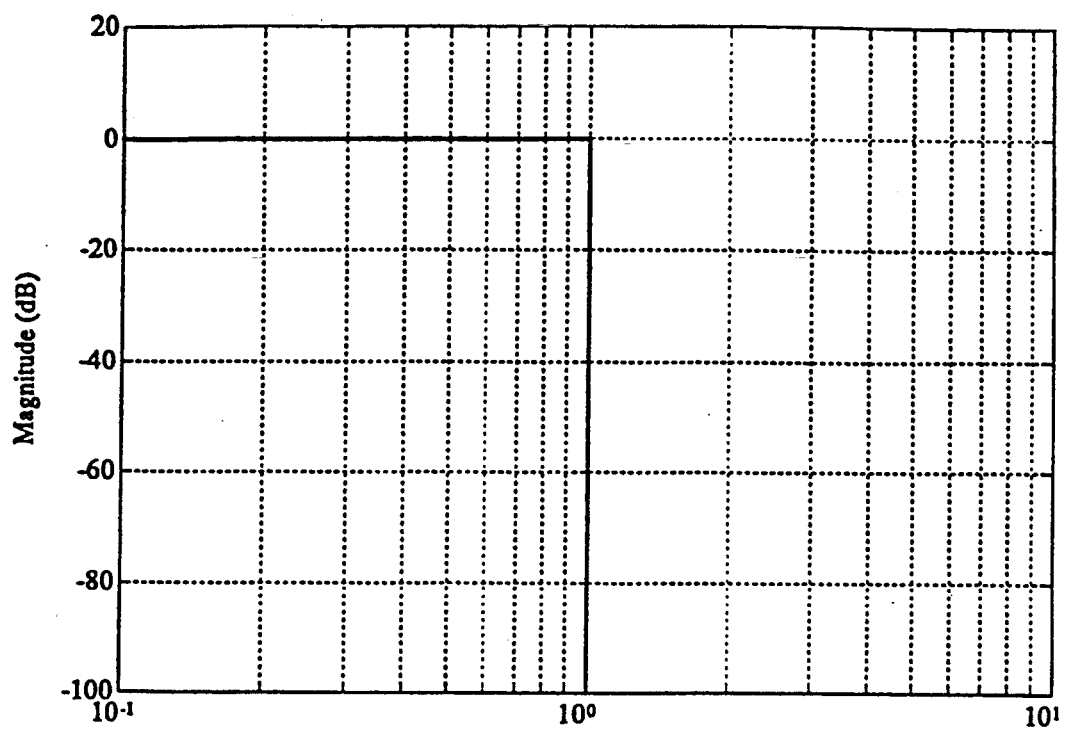
FIGS. 16-18 illustrate transfer functions and phase for the sensor weightings of FIGS. 7-9.
Figure 16B:
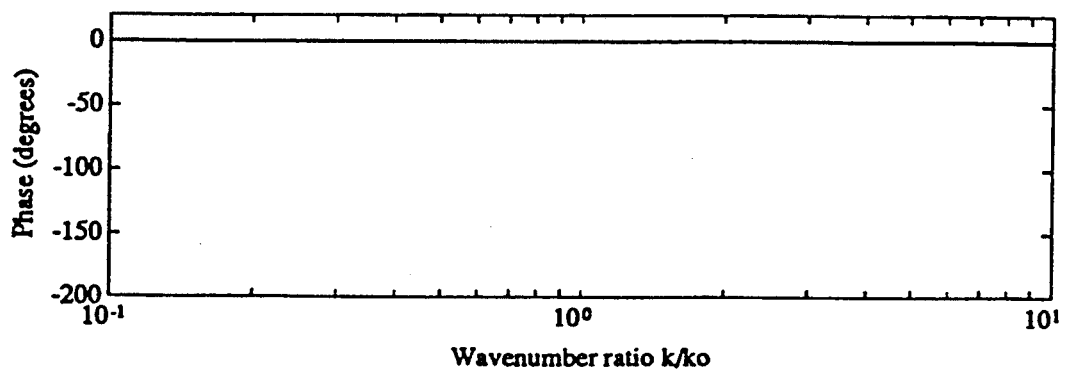

A Sinc sensor is an example of a sensor which satisfies some, but not all the functional requirements outlined above. Its weighting is that of a Sinc function, and its transfer function is like a perfect lowpass filter. The magnitude of this transfer function is unity for all frequencies below the cutoff, and zero at all frequencies above the cutoff. The magnitude immediately drops from unity to zero at the cutoff frequency, and no phase lag is introduced. This is seen to satisfy the second sensor objective but since the weighting is negative for some values of x, the eighth objective is not satisfied. In addition, the seventh objective is not satisfied either. The transfer function and phase of the Sinc weighting is the perfect lowpass filter shown in FIG. 16. It is defined by $$F(k) = \frac{1 + \text{sgn}(1 - \bar{k})}{2} \tag{2.58}$$

where $k = k/\alpha$. The parameter $\alpha$ introduced in (2.15) is used to define the spatial frequency k at which the sensor rolls off. In this case, roll off occurs at exactly $k = 1$, or when $k = \alpha$.

The transfer function is unity for all wave numbers k less than the cutoff wave number, and zero for all k above it. The transition from perfect transmission to perfect impedance is instantaneous, and no phase lag is introduced. This behavior is only exhibited by a Sinc weighting that extends over an infinite domain. For implementation to be possible, the sensor must be spatially truncated at the boundaries of the structure. Such a truncated sensor can accurately observe modes in the bandwidth and will roll off relatively fast, satisfying the second requirement. However, the magnitude rolloff of the output of the truncated sensor contains negative regions, where the sign of the output of the sensor is opposite to that of the strain at the center of the sensor. In space, truncation is a multiplication of the sensor weighting by a rectangular weighting. In the wave number domain, the Fourier transform of the truncated sensor is the result of convolving the perfect low pass filter with the transfer function of the rectangular weighing. The result contains negative regions, i.e.,
regions where the phase has shifted by ±180°, violating the third desired sensor property.

Figure 17B:
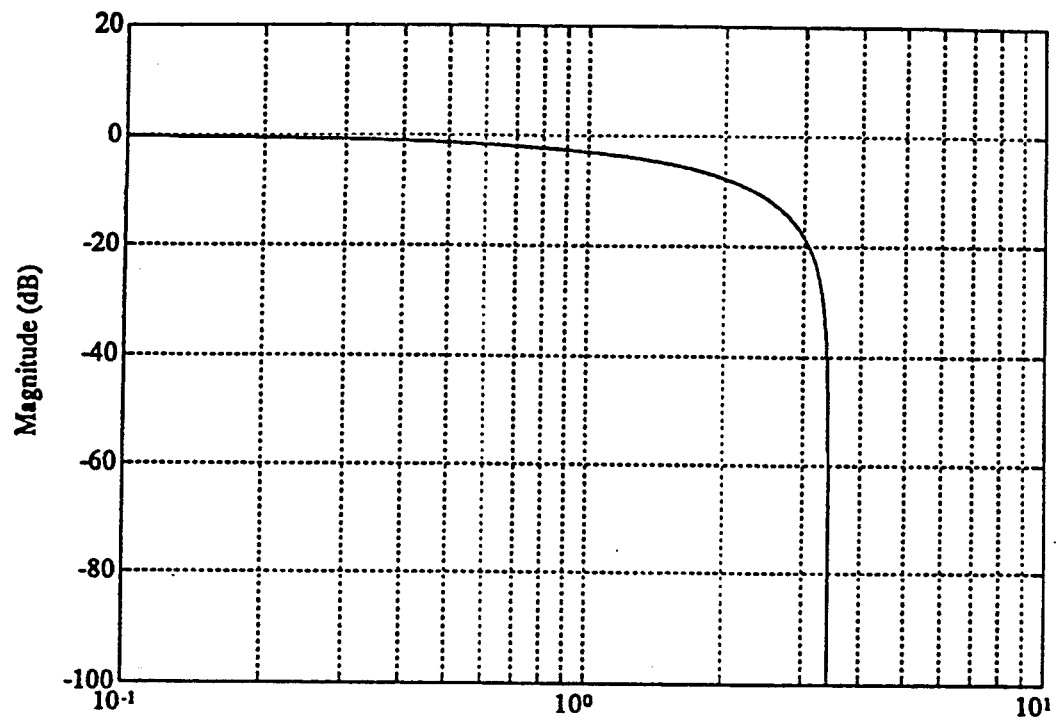
Figure 17B:
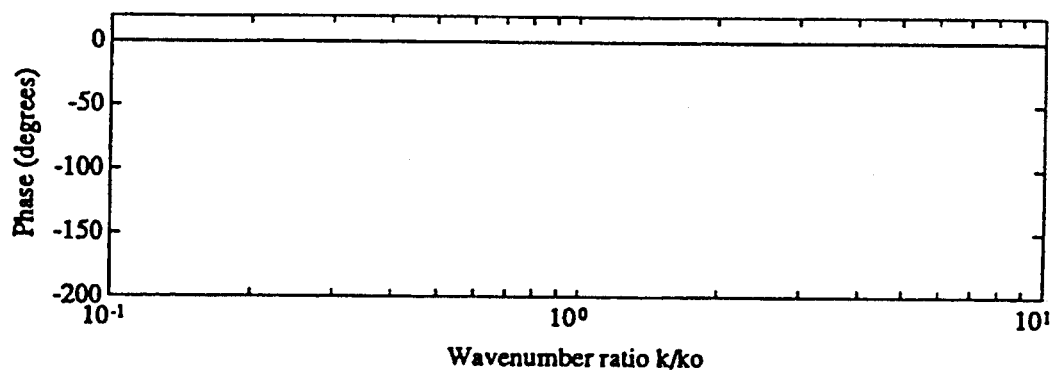

Since the Sinc-Sinc weighting is obtained by multiplying two Sinc functions together, it follows that the transfer function for the Sinc-Sinc weighting must be the convolution of the transfer functions of two Sinc functions. Thus the transfer function of the Sinc-Sinc weighting is triangular. It is shown i FIG. 17 and is given by:

$$T(k) \begin{cases} 1 - \frac{\bar{k}}{2 + \sqrt{2}} & \bar{k} < 2 + \sqrt{2} \\ 0 & \bar{k} \geq 2 + \sqrt{2} \end{cases} \tag{2.59}$$

The Sinc-Sinc weighting was investigated because it does not require regions of negative sensitivity, and yet yields excellent performance. As with the Sinc weighting, it suffers from the fact that it must be spatially truncated for the purposes of implementation.

In general, the side lobes can be reduced by having the ends of the weighting approach zero more and more smoothly. This is shown in Equation (2.40) and in Table II in that the rolloff rate is faster as higher and higher derivatives of the weighting function f(x) are zero at the ends. A Gaussian is infinite in length and can be shown to approach zero infinitely smoothly as x approaches ±∞. The transfer function of a Gaussian is also a Gaussian:

$$T(k) = \exp\left(-\frac{\ln 2}{2} \bar{k}^2\right) \tag{2.60}$$

Figure 18B:
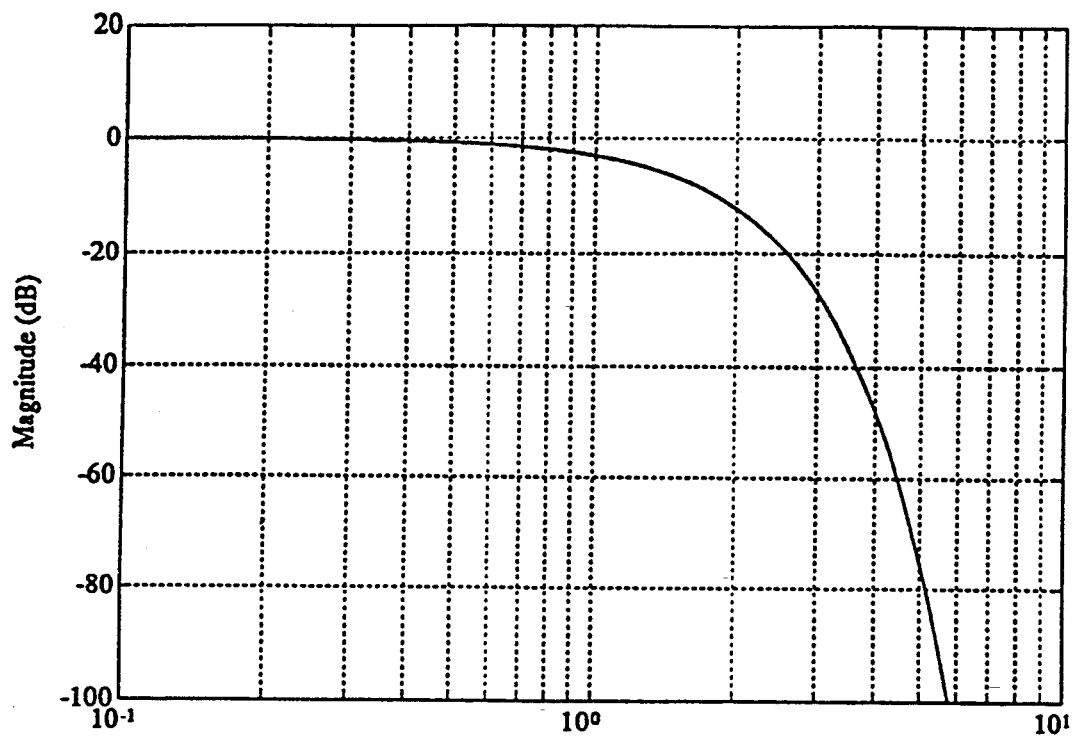
Figure 18B:
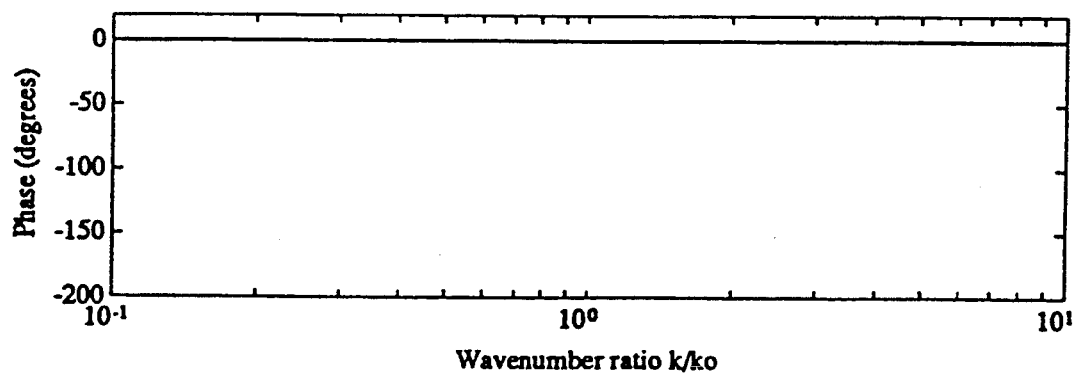

FIG. 18 shows the magnitude and phase of the transfer function for a Gaussian weighting. It can be seen from this plot and (2.60), that the transfer function of a Gaussian sensor has no side lobes at all, and the rolloff becomes increasingly fast. In fact, at k-oo the rolloff is infinite, as predicted in Table IV. As shown in (2.60), the magnitude is everywhere nonnegative, implying that the transfer function of the Gaussian weighting will not exhibit any phase lag. Note again that the Gaussian weighting must be spatially truncated for implementation purposes.

The transfer function of the Bartlett-Bartlett weighting is derived from (2.45). From (2.21) it is clear that all derivatives $f^{(i)}(x)$ for $i > 2$ are zero. Thus (2.45) simplifies to $$T(k) = \frac{1}{k} [f(-l/2) + f(l/2)]\sin(kl/2) + \tag{2.61}$$

$$\frac{1}{k^2} [f'(0^-) - f'(0^+) + [-f'(-l/2) + f'(l/2)]\cos(kl/2)] +$$

$$\frac{1}{k^3} [-f''(-l/2) - f''(l/2)](\sin(kl/2))$$

Knowing that for the Bartlett-Bartlett weighting $f(-\frac{1}{2}) = f(\frac{1}{2})0$, $f'(-\frac{1}{2}) = f'(\frac{1}{2}) = 0$, $f'(0-) = -f'(0+) = 3\alpha^2/\pi^2$, $f''(-\frac{1}{2}) = f''(\frac{1}{2}) = 3\alpha^3/\pi^3$, and $l/2 = \pi/\alpha$, the expression for the transfer function simplifies to $$T(k) = \frac{1}{k^2}\left(\frac{3a^2}{\pi^2} + \frac{3a^2}{\pi^2}\right) + \quad (2.62)$$

$$\frac{1}{k^3}\left(-\frac{3a^3}{\pi^3} + \frac{3a^3}{\pi^3}\right)\sin\frac{k\pi}{a}$$

$$T(k) = \frac{6a^2}{\pi^2 k^2} - \frac{6a^3}{\pi^3 k^3}\sin\frac{k\pi}{a} \quad (2.63)$$

Using $\bar{k} = k/a$, we find $$T(k) = 6\left(\frac{\pi\bar{k} - \sin(\pi\bar{k})}{(\pi\bar{k})^3}\right) \quad (2.64)$$

Figure 19B:
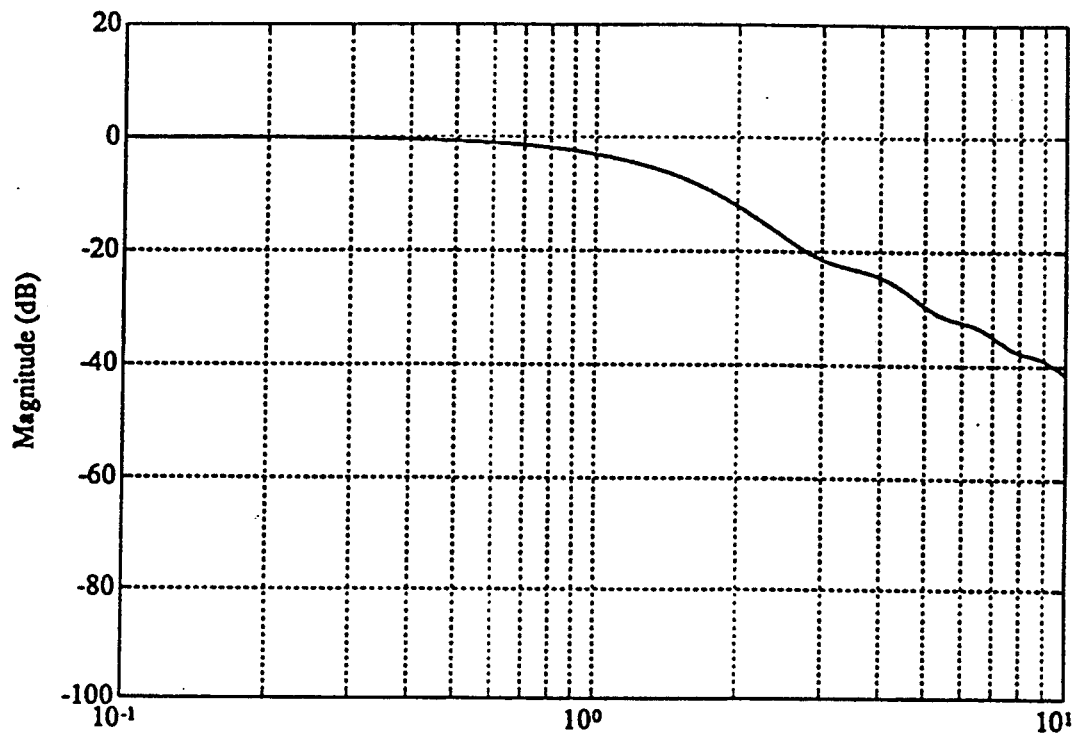
FIGS. 19-21 illustrate transfer functions and phase for the sensor weightings of FIGS. 10-12.
Figure 19B:
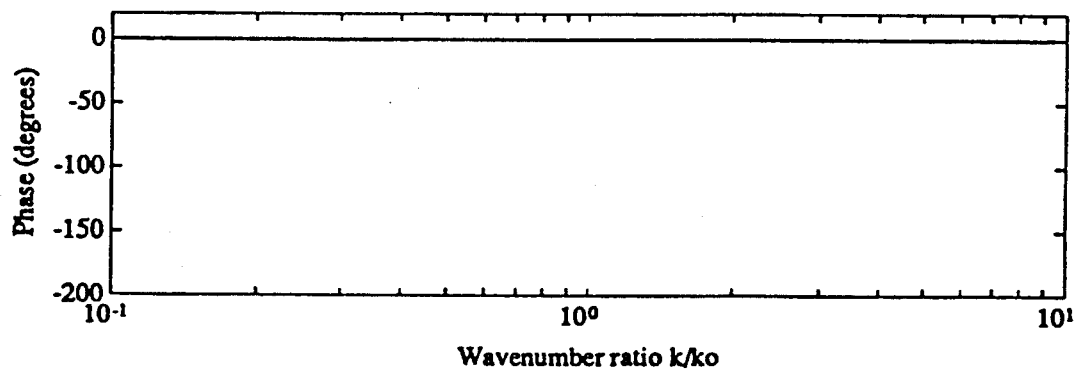

FIG. 19 shows the magnitude and phase of the transfer function for the Bartlett-Bartlett weighting. As with the Bartlett weighting, the Bartlett-Bartlett weighting provides a rolloff rate of only $1/k^2$, as predicted in Table IV. However, unlike the Bartlett weighting, the transfer function of the Bartlett-Bartlett weighting approaches zero monotonically as k approaches infinity. Thus it possesses no side lobes or zeros, and introduces no phase lag.

In order to improve the side lobe structure of the Hanning weighting, the Hanning-Hanning weighting was created by multiplying two Manning weightings together. This has the effect of convolving the transfer functions of two Henning weightings. The transfer function is given by $$T(k) = \frac{2}{3}\frac{\sin(\pi(\bar{k}+1))}{\pi(\bar{k}+1)} + \frac{2}{3}\frac{\sin(\pi(\bar{k}-1))}{\pi(\bar{k}-1)} + \quad (2.65)$$

$$\frac{1}{6}\frac{\sin(\pi(\bar{k}+2))}{\pi(\bar{k}+2)} + \frac{1}{6}\frac{\sin(\pi(\bar{k}-2))}{\pi(\bar{k}-2)} + \frac{\sin\pi\bar{k}}{\pi\bar{k}}$$

Figure 20B:
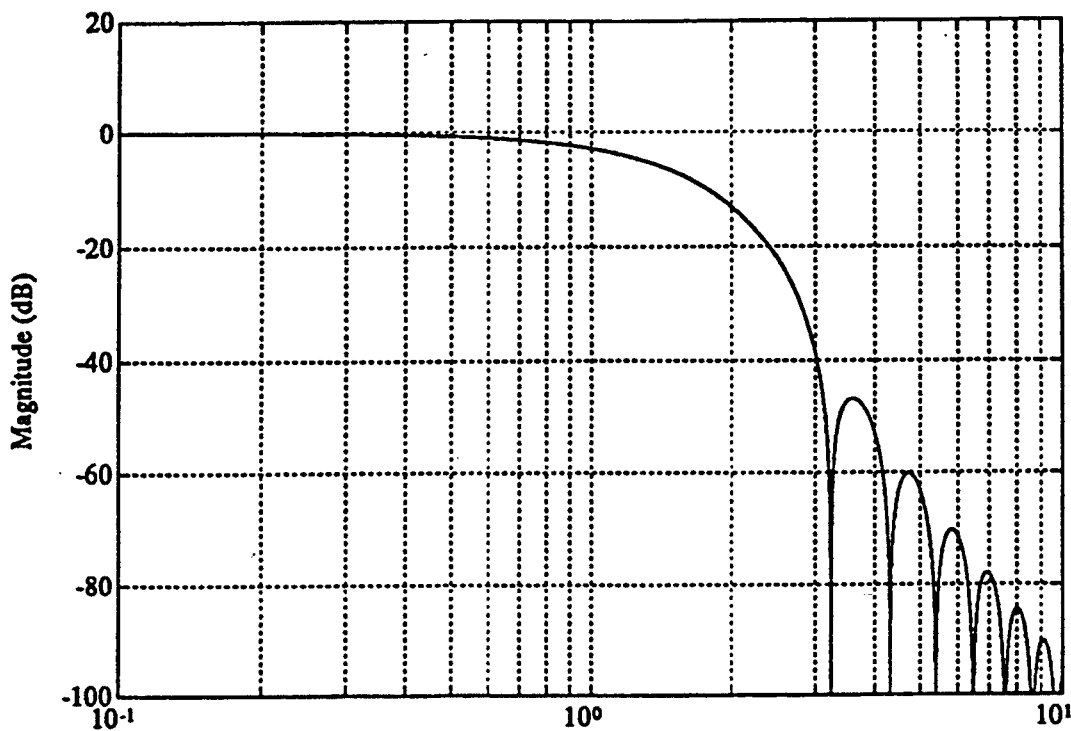
Figure 20B:
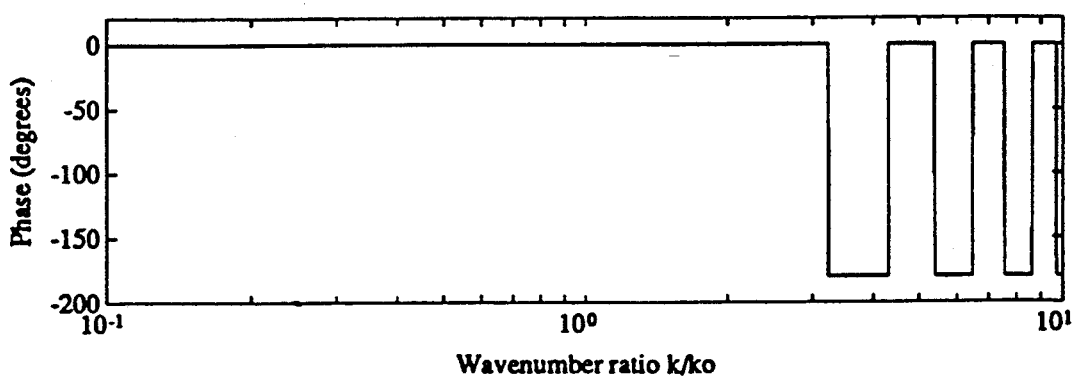

The magnitude and phase of the transfer function for the Hanning-Hanning weighting is shown in FIG. 20. It can be seen the rolloff rate has been increased to $-100$ dB/decade, as predicted in Table IV. The sign reversals at the zeros of the transfer function can be seen in the phase plot. The height of the first side lobe has been decreased to $-46.74$ dB, an improvement over the simple Hanning weighting. It can be seen that the improvement in rolloff rate and side lobe height has come at the expense of a spatially longer weighting.

Figure 21B:
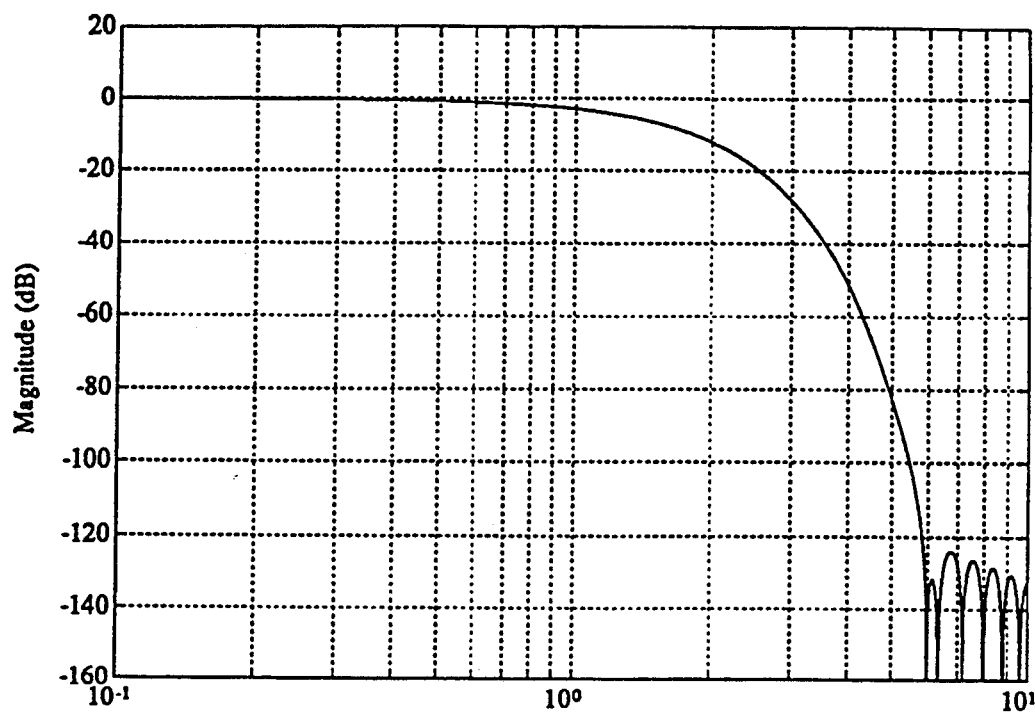
Figure 21B:
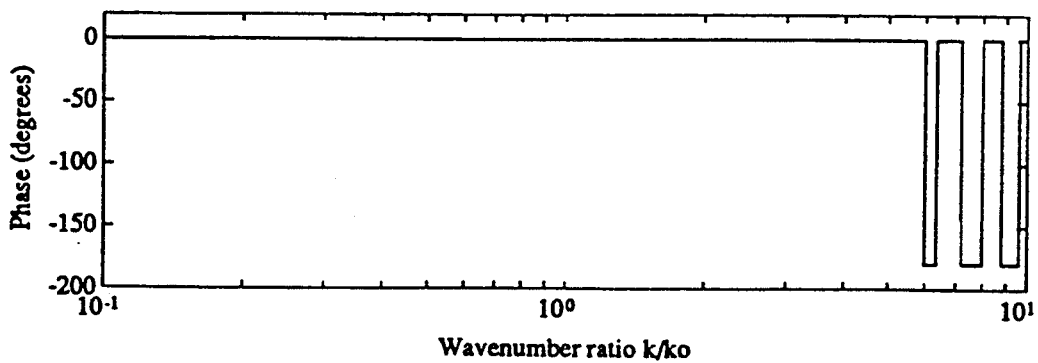

In an effort to obtain a finite weighting with rapid rolloff, a Gaussian weighting was made finite by truncating it smoothly with a Hanning weighting. The result is a weighting that has very good rolloff in the decade beyond the rolloff point and yet is finite. The magnitude and phase of the transfer function is shown in FIG. 21. The analytic expression for the transfer function is highly complex. As predicted in Table IV, the magnitude eventually rolls off at the same rate as a simple Hanning window, $1/k^3$.

TABLE V

Frequency properties of selected strain-averaging sensors.

| Sensor Weighting | Rolloff in first decade (dB) | Rolloff rate (dB/decade) | Negatives in k? | Several zeroes? | First side lobe height (dB) |
|---|---|---|---|---|---|
| Rectangle | $-20$ | $-20$ | No | Yes | $-13.26$ |
| Bartlett | $-40$ | $-40$ | Yes | Yes | $-26.52$ |
| Hanning | $-60$ | $-60$ | No | Yes | $-31.47$ |
| Sinc | $-\infty$ | $-\infty$ | Yes | No | — |
| Sinc-Sinc | $-\infty$ | $-\infty$ | Yes | No | — |
| Gauss | $-300$ | $-28$ | Yes | No | — |
| Bartlett-Bartlett | $-40$ | $-40$ | Yes | No | — |
| Hanning-Hanning | $-100$ | $-100$ | No | Yes | $-46.74$ |
| Gauss-Hanning | $-140$ | $-60$ | No | No | $-131.83$ |

At this point the properties of the transfer functions of the weightings are summarized. Table V summarizes the actual spatial frequency properties of the selected weighting functions introduced earlier. In the second column, the rolloff point is defined as the $-3$ dB point, where the magnitude of the transfer function has fallen to $1/\sqrt{2}$, and the rolloff in the first decade is estimated from the magnitude decrease in one decade beyond the rolloff wave number. The Sinc, Gaussian and Sinc-Sinc weightings yield the most rolloff within one decade up from the $-3$ dB point, and yield infinite rolloff rate far above the rolloff point. The Gauss-Hanning weighting approaches this performance, and is spatially finite and thus implementable without further spatial truncation. Thus it satisfies requirements 2, 7 and 8. However, it's eventual rolloff rate is that of a Hanning weighting, as predicted in Table IV. The third column gives the rolloff rate the transfer function exhibits far above the rolloff point. The fourth column indicates whether the transfer function of the weighting contains any negative portions. From the functional requirements, such negative regions should be avoided in order to avoid instabilities in a control system using spatially averaging strain sensor measurements. The fifth column shows whether there are multiple zeros in the transfer function. Those that do not have multiple zeros have one at $k=\infty$. It should be noted that transfer functions of the Sinc and Sinc-Sinc weightings go to zero at a finite value of k and remain zero for all larger values of k. The last column shows the height of the first side lobe, when such a lobe exists. It is known that the size or height of the side lobes determines the amount of leakage the window suffers. It is responsible for ripples in the pass- and stopbands of the sensor's transfer function T(k).

This completes a description of representative sensor weightings and their spatial transfer functions for centered sensors.

Being able to center a sensor at the point of symmetry in a strain field represents an ideal condition. In general, sensors are not placed at such ideal locations. Therefore, the output of a sensor mounted in the interior of a structure, away from its boundaries, centered at a distance $x_o$ from the point of symmetry in a sinusoidal strain field is also discussed herein. It is now assumed that the strain field is spatially sinusoidal and of the form $$\epsilon(\chi) = \sin(k\chi) \qquad (2.66)$$

where k is the wave number. The output of a sensor with weighting function f(x), centered at $x=x_o$ is then given by $$y(k) = \int_{-l/2 + x_o}^{l/2 + x_o} f(x - x_o)\sin(kx)dx \qquad (2.67)$$

By repeatedly integrating this expression by parts, an infinite series solution for the output of a sensor mounted in the interior of a structure) away from its boundaries, centered at a distance xo from the point of symmetry in a sinusoidal strain field can be written as $$y(k) = \sum_{i=0}^{\infty} \left\{ \frac{(-1)^i}{k^{(2i+1)}} [-f^{(2i)}(l/2)\cos[k(l/2 + x_o)] + f^{2i}(-l/2)\cos[k(-l/2 + x_o)]] + \frac{(-1)^i}{k^{(2i+2)}} [f^{(2i+1)}(l/2)\sin[k(l/2 + x_o)] - [f^{(2i+1)}(-l/2)\sin[k(-l/2 + x_o)]]] \right\} \qquad (2.68)$$

To obtain the transfer function from the strain at the center of the sensor to its output, (2.68) must be divided by the strain at the center of the sensor $\sin(kx_\cap)$:

$$T(k) = \sum_{i=0}^{\infty} \left\{ \frac{(-1)^i}{k^{(2i+1)}} \left[ \frac{-f^{(2i)}(l/2)\cos[k(l/2 + x_o)] + f^{(2i)}(-l/2)\cos[k(-l/2 + x_o)]}{\sin(kx_o)} \right] + \frac{(-1)^i}{k^{(2i+2)}} \left[ \frac{f^{(2i+1)}(l/2)\sin[k(l/2 + x_o)] - f^{(2i+1)}(-l/2)\sin[k(-l/2 + x_o)]}{\sin(kx_o)} \right] \right\} \qquad (2.69)$$

This expression may be simplified by expanding sine and cosine terms, leaving $$T(k) = \sum_{i=0}^{\infty} \left\{ \frac{(-1)^i}{k^{(2i+1)}} \left[ -f^{(2i)}(l/2)\left(\frac{\cos(kl/2)}{\tan(kx_o)} - \sin(kl/2)\right) + f^{(2i)}(-l/2)\left(\frac{\cos(kl/2)}{\tan(kx_o)} + \sin(kl/2)\right) \right] + \frac{(-1)^i}{k^{(2i+2)}} \left[ f^{(2i+1)}(l/2)\left(\frac{\sin(kl/2)}{\tan(kx_o)} + \cos(kl/2)\right) - f^{(2i+1)}(-l/2)\left(-\frac{\sin(kl/2)}{\tan(kx_o)} + \cos(kl/2)\right) \right] \right\} \qquad (2.70)$$

If the sensor is symmetric, (2.70) simplifies to (2.43), showing that the transfer function between the strain at the center or the sensor and-its output is independent of $x_o$, and hence of where the sensor is centered. Using the identities (2.41) and (2.42) that are valid when f(x) is symmetric, (2.70) is simplified to the form $$T(k) = \sum_{i=0}^{\infty} \left\{ \frac{(-1)^i}{k^{(2i+1)}} \left[ -f^{(2i)}(l/2)\left(\frac{\cos(kl/2)}{\tan(kx_o)} - \sin(kl/2)\right) + f^{(2i)}(-l/2)\left(\frac{\cos(kl/2)}{\tan(kx_o)} + \sin(kl/2)\right) \right] + \frac{(-1)^i}{k^{(2i+2)}} \left[ f^{(2i+1)}(l/2)\left(\frac{\sin(kl/2)}{\tan(kx_o)} + \cos(kl/2)\right) + f^{(2i+1)}(l/2)\left(-\frac{\sin(kl/2)}{\tan(kx_o)} + \cos(kl/2)\right) \right] \right\} \qquad (2.71)$$

which further simplifies to $$T(k) = \sum_{i=0}^{\infty} \left\{ \frac{2(-1)^i}{k^{(2i+1)}} f^{(2i)}(l/2)\sin(kl/2) + \frac{2(-1)^i}{k^{(2i+2)}} f^{(2i+1)}(l/2)\cos(kl/2) \right\} \qquad (2.72)$$

This expression is clearly the same as (2.40) indicating that the transfer function is indeed independent of $x_o$ as long as f(x) is symmetric.

This result can also be derived for weightings containing a derivative discontinuity, such as the Bartlett weighting. For such a weighting, (2-67) is first modified:

$$y(k) = \int_{-l/2 + x_o}^{x_o^-} f(x - x_o)\sin(kx)dx + \int_{x_o^+}^{l/2 + x_o} f(x - x_o)\sin(kx)dx \qquad (2.73)$$

where $x_o^-$ is a point just before the discontinuity in f(x), and $x_o^+$ is a point just after it. Equation (2.73) is integrated repeatedly to obtain:

$$y(k) = \sum_{i=0}^{\infty} \left\{ \frac{(-1)^i}{k^{(2i+1)}} \left[ -f^{(2i)}(l/2)\left(\frac{\cos(kl/2)}{\tan(kx_o)} - \sin(kl/2)\right) + f^{(2i)}(-l/2)\left(\frac{\cos(kl/2)}{\tan(kx_o)} + \sin(kl/2)\right) \right] + \frac{(-1)^i}{k^{(2i+2)}} \left[ f^{(2i+1)}(l/2)\left(\frac{\sin(kl/2)}{\tan(kx_o)} + \cos(kl/2)\right) - f^{(2i+1)}(-l/2)\left(-\frac{\sin(kl/2)}{\tan(kx_o)} + \cos(kl/2)\right) \right] \right\} \qquad (2.74)$$

Assuming f(x) is symmetric, and expanding the trigonometric terms, (2.74) simplifies to $$y(k) = \sum_{i=0}^{\infty} \left\{ \frac{2(-1)^i}{k^{(2i+1)}} [f^{(2i)}(l/2)\sin(kl/2)]\sin(kx_0) + \right. \tag{2.75}$$

$$\left. \frac{2(-1)^i}{k^{(2i+2)}} [f^{(2i+1)}(l/2)\cos(kl/2) - f^{(2i+1)}(0^+)]\sin(kx_0) \right\}$$

The transfer function is then obtained by dividing (2.75) by $\sin(kx_o)$ to obtain $$y(k) = T(k) = \sum_{i=0}^{\infty} \left\{ \frac{2(-1)^i}{k^{2i+1}} f^{(2i)}(-l/2)\sin(kl/2) + \right. \tag{2.76}$$

$$\left. \frac{2(-1)^i}{k^{2i+2}} [f^{(2i+1)}(l/2)\cos(kl/2) - f^{(2i+1)}(0^+)] \right\}$$

It can be seen that this is exactly the same as (2.46), thus showing that the transfer function of a weighting with a derivative discontinuity is independent of $x_o$, and therefore of where the sensor is placed relative to the point of symmetry in the strain field. In addition, this shows that the sensor transfer function is the same, no matter whether the strain field is assumed to be spatially sinusoidal or cosinusoidal, proving that the since and cosine transforms of a spatially symmetric weighting function are the same.

In distributing an array of sensors on a structure, sensors will inevitably have to be placed in such a way as to cause some portion of the sensor weighting to fall beyond a boundary of the structure. This portion must be truncated in the implementation of the sensor. The frequency characteristics of the transfer function of a sensor are changed dramatically if a portion of the sensor is truncated at a boundary of the structure. The output of a sensor mounted near a boundary of a structure, at a distance $x_o$ from the point of symmetry in a sinusoidal strain field is therefore investigated. It is again assumed that the strain field is of the form $$\epsilon(\chi) = \sin(k\chi) \tag{2.77}$$

where k is the wave number. It is further assumed that the boundary of the structure is at $x=0$. The output of a sensor with weighting function f(x), centered at $x=x_o$ is then given by $$y(k) = \int_0^{x_0 + l/2} f(x - x_0)\sin(kx)dx \tag{2.78}$$

Figure 22:
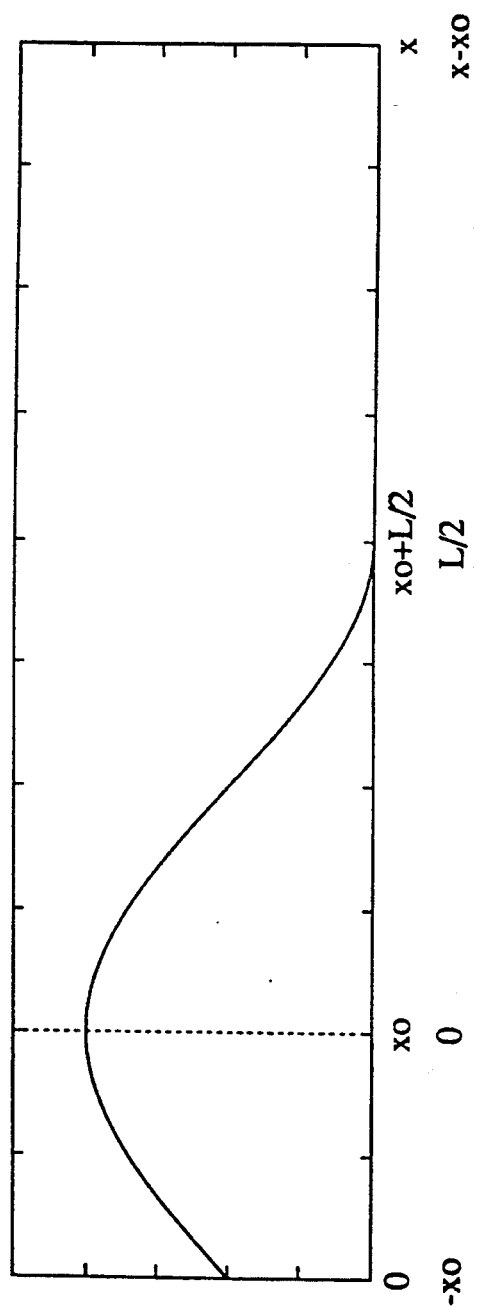
FIG. 22 illustrates the weighting of a truncated sensor.

FIG. 22 shows a schematic of a sensor truncated at a boundary of the structure. Such a truncated weighting must be scaled such that low spatial frequency signals are measured correctly. This is accomplished by requiring that $$\int_0^{l/2 + x_0} f(x - x_0)\,dx = 1 \tag{2.79}$$

The upper horizontal axis system in FIG. 22 is the axis of the structure, where the boundary has been set at $x=0$. The lower horizontal axis is relative to the sensor, where $x=0$ has been set at the center of the sensor. The distance between these two points is $x_o$. By integrating (2.78) by parts repeatedly, an infinite series solution for the output of a sensor mounted in the interior of a structure, away from its boundaries, centered at a distance $x_o$ from the point of symmetry in a sinusoidal strain field can be written as $$y(k) = \sum_{i=0}^{\infty} \left\{ \frac{(-1)^i}{k^{(2i+1)}} [-f^{(2i)}(l/2)\cos[k(l/2 + x_0)] + f^{(2i)}(-x_0)] + \right. \tag{2.80}$$

$$\left. \frac{(-1)^i}{k^{(2i+2)}} [f^{(2i+1)}(l/2)\sin[k(l/2 + x_0)]] \right\}$$

Equation (2.80) is divided by $\sin(kx_o)$ in order to obtain the transfer function for a sensor truncated at a structure boundary in a sinusoidal strain field. This yields $$T(k) = \sum_{i=0}^{\infty} \left\{ \frac{(-1)^i}{k^{(2i+1)}} \left[ -f^{(2i)}(l/2) \left( \frac{\cos(kl/2)}{\tan(kx_0)} - \sin(kl/2) \right) + \right. \right. \tag{2.81}$$

$$f^{(2i)}(-x_0) \left( \frac{1}{\sin(kx_0)} \right) \right] +$$

$$\left. \frac{(-1)^i}{k^{(2i+2)}} \left[ f^{(2i+1)}(l/2) \left( \frac{\sin(kl/2)}{\tan(kx_0)} + \cos(kl/2) \right) \right] \right\}$$

The term $f^{(2i)}(-x_o)$ is the value of the weighting and all its even derivatives at the boundary of the structure. While the $f^{(2i)}(\pm\frac{l}{2})$ terms are generally zero for low values of i, the $f^{(2i)}(-x_o)$ terms are not. Therefore, the rolloff of the transfer function (2.81) is limited to 1/k. The presence of the $\tan(kx_o)$ and $\sin(kx_o)$ terms in the denominator means that the transfer function T(k) is no longer bounded in amplitude, even when f(x) is symmetric. This is simply because the sensor is no longer symmetric in its truncated state and can report a nonzero strain even when the strain at its center, $x=x_o$, is zero.

Figures 23A, 23B:
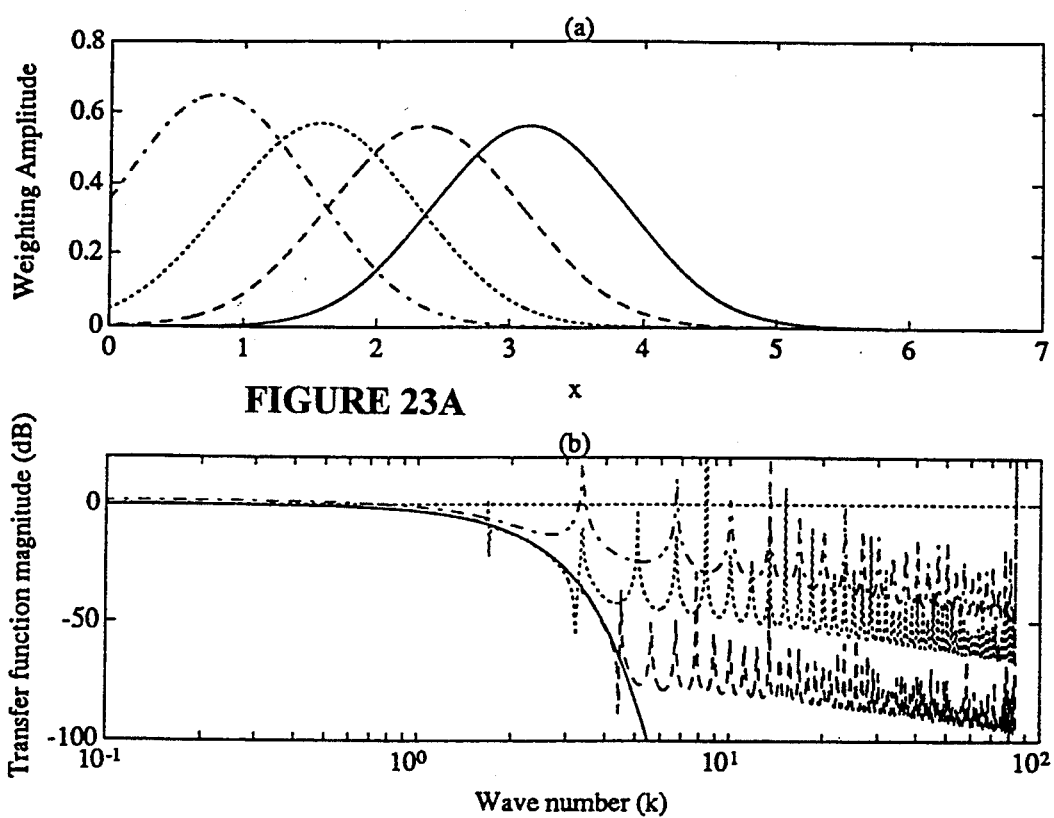
FIG. 23 illustrates the weighting function and corresponding spatial transfer function of a Gauss-Hanning sensor truncated as in FIG. 22, as a function of truncation length.

FIG. 23 shows the effect of sensor truncation on rolloff behavior of the sensor transfer function T(k). The Figure shows a series of four sensors with Gauss-Hanning weightings. The first sensor, shown in a solid line, is not truncated. The next three, shown in dashed, dotted and dot-dashed lines respectively, are more and more drastically truncated. FIG. 23B shows the transfer functions for the untruncated and three truncated sensors. It is clear that as soon as the sensor is truncated by any small amount, the long-term rolloff rate becomes 1/k. As more and more of the sensor is truncated, the average magnitude of T(k) beyond the rolloff point increases. Finally, it is clear that the transfer functions of the truncated sensors are no longer bounded in amplitude.

In an effort to assure that boundary truncation does not impair sensor utility, a powerful truncation technique which improves the rolloff behavior of the truncated sensor is next described.

Figure 24:
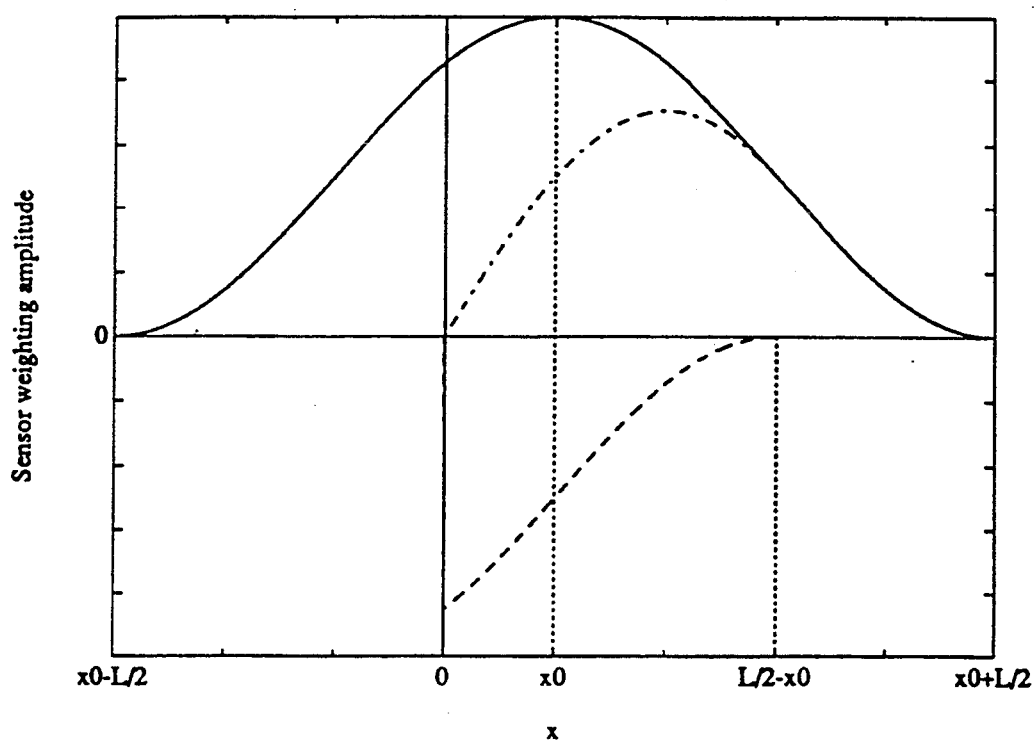
FIG. 24 illustrates a technique of this invention for modifying weightings at sensor boundaries.

Applicant has observed that the frequency characteristics of a sensor are very interesting when the portion of the weighting function beyond the structure boundary is folded over about the boundary and subtracted from the remaining interior portion of the sensor weighting. FIG. 24 shows this procedure.

The solid line shows the weighting of an untruncated sensor that extends beyond the boundary of the structure which is assumed to be at x=0. The dashed line shows the truncated portion of the sensor after being reflected about the boundary of the structure and then made negative. This part is then added to the untruncated part of the original sensor. The resulting truncated sensor weighting is shown by the dot-dashed line. The frequency characteristics of this modified sensor are investigated next. The output of the modified sensor is given by $$y(k) = \int_0^{l/2 - x_0} [f(x - x_0) - f(-x - x_0)]\sin(kx)dx + \int_{l/2 - x_0}^{l/2 + x_0} f(x - x_0)\sin(kx)dx \quad (2.82)$$

Note that we will require that $$\int_{-l/2 + x_0}^{l/2 + x_0} f(x - x_0) dx = 1 \quad (2.83)$$

That is, the area of the original sensor is unity. Note that no further scaling of f(x) is performed. The weighting $f(-x-x_o)$ is the original weighting $f(x-x_o)$ reflected about the boundary of the structure at x=0. The length of the portion of the sensor that extends beyond the boundary of the sensor is $l/2 - x_o$. Equation (2.82) can be rewritten $$y(k) = \int_0^{l/2 + x_0} f(x - x_0)\sin(kx)dx - \int_0^{l/2 - x_0} f(-x - x_0)\sin(kx)dx \quad (2.84)$$

$$y(k) = G(k) - H(k) \quad (2.85)$$

The first integral G(k) in (2.84) was dealt with in the previous section and the result is shown in (2.80). By repeated integration by parts, H(k) can be written as an infinite series in the following manner:

$$H(k) = \sum_{i=0}^{\infty} \left\{ \frac{(-1)^i}{k^{(2i+1)}} [-f^{(2i)}(-l/2)\cos[k(l/2 - x_0)] + f^{(2i)}(-x_0)] + \frac{(-1)^i}{k^{(2i+2)}} [-f^{(2i+1)}(-l/2)\sin[k(l/2 - x_0)]] \right\} \quad (2.86)$$

By subtracting this expression for H(k) from (2.80), the output of the modified sensor as a function of frequency can be found to be $$y(k) = \sum_{i=0}^{\infty} \left\{ \frac{(-1)^i}{k^{(2i+1)}} [-f^{(2i)}(l/2)\cos[k(l/2 + x_0)] + f^{(2i)}(-l/2)\cos[k(-l/2 + x_0)]] + \frac{(-1)^i}{k^{(2i+2)}} [f^{(2i+1)}(l/2)\sin[k(l/2 + x_0)] - \quad (2.87) \right. $$

$$\left. f^{(2i+1)}(-l/2)\sin[k(-l/2 + x_0)]] \right\}$$

It can be seen that this expression is the same as (2.68). Therefore, the transfer function for such a sensor will be the same as (2.70):

$$T(k) = \sum_{i=0}^{\infty} \left\{ \frac{(-1)^i}{k^{(2i+1)}} \left[ -f^{(2i)}(l/2) \left( \frac{\cos(kl/2)}{\tan(kx_0)} - \sin(kl/2) \right) + \right.\right. \quad (2.88)$$

$$\left. f^{(2i)}(-l/2) \left( \frac{\cos(kl/2)}{\tan(kx_0)} + \sin(kl/2) \right) \right] +$$

$$\frac{(-1)^i}{k^{(2i+2)}} \left[ f^{(2i+1)}(l/2) \left( \frac{\sin(kl/2)}{\tan(kx_0)} + \cos(kl/2) \right) - \right.$$

$$\left.\left. f^{(2i+1)}(-l/2) \left( -\frac{\sin(kl/2)}{\tan(kx_0)} + \cos(kl/2) \right) \right] \right\}$$

In addition, the transfer function of an originally symmetric sensor which has been truncated by this folding approach is the same as (2.72):

$$T(k) = \sum_{i=0}^{\infty} \left\{ \frac{2(-1)^i}{k^{(2i+1)}} f^{(2i)}(l/2)\sin(kl/2) + \frac{2(-1)^i}{k^{(2i+2)}} f^{(2i+1)}(l/2)\cos(kl/2) \right\} \quad (2.89)$$

This result shows that sensors truncated with this 'folding' technique enjoy the same properties as untruncated sensors provided the strain field is assumed to be sinusoidal. This is true regardless of whether the original weighting f(x) is symmetric or not.

In summary for a centered sensor whose center is placed at the point of symmetry in a cosinusoidal strain field, its transfer function is the same as the spatial Fourier transform, provided that f(x) is symmetric; that is, if $f(x)=f(-x)$. In the limit as $x_\sigma\rightarrow\infty$, the transfer function for a symmetric, centered sensor in a sinusoidal field is also equal to the spatial Fourier transform. The rolloff rate of the sensor transfer function is governed by how smoothly f(x) tapers to zero at the ends ($x=\pm\frac{l}{2}$). The more smoothly f(x) goes to zero the more derivatives of f(x) are zero at the ends. Table II shows this behavior. Generally, as the weighting tapers more smoothly to zero, its length must necessarily increase in order to roll off at the same spatial frequency. In addition, the transition band of the transfer function increases, and the side lobe structure is reduced in height.

For a noncentered sensor whose center is a distance $x_o$ from the point of symmetry in a sinusoidal strain field, similar properties hold. As the weighting is tapered more smoothly to zero, the rolloff rate increases in the same way as for a centered sensor. If f(x) is not symmetric, the transfer function will not be bounded in amplitude. If f(x) is symmetric, however, the transfer function is bounded in amplitude and becomes independent of $x_o$, and equal to the transfer function for a centered sensor.

When a sensor is truncated, its rolloff performance decreases drastically, in proportion to the fraction of the sensor weighting which is truncated. The transfer function is no longer bounded in amplitude because the truncated weighting is no longer symmetric. In addition, the rolloff rate decreases to 1/k no matter how smoothly the weighting tapers to zero at the ends because the value of the weighting at the structure boundary is nonzero in general.

This truncation technique of 'folding' the portion of the weighting that falls beyond the boundary was introduced to improve sensor rolloff performance and better satisfy the second and ninth desired sensor properties discussed above. In a sinusoidal strain field, the transfer function of untruncated sensors and sensors truncated with this technique are identical whether f(x) is symmetric or not.

The modeshapes of structures are generally composed of sinusoidal and exponential-like functions. The properties of sensors in sinusoidal and cosinusoidal strain fields were analyzed above. In the following description, the properties of sensors in an exponential strain field are investigated.

The exponential strain fields are assumed to have the form $e^{-kx}$. The origin will refer to the point where the strain remains the same no matter what the spatial frequency is. For the strain field $e^{-kw}$, this point is simply $x=0$, where the strain is unity for all k. It is important to note that k is not a spatial frequency as it is for the strain field sin(kx) because $e^{-kx}$ is not oscillatory. Rather, k is a scale length that determines how quickly the strain field tapers toward zero for positive x. Since the strain field is not oscillatory, the properties of the transfer functions will not resemble those described for sinusoidal curvature. Further, since modeshapes are generally spatially oscillatory, it is of limited use to analyze the properties of the transfer function of sensors in a purely exponential strain field. The form of the exponential near-field terms in the modeshapes of structures should be considered when examining the following results.

The output of a sensor mounted on a structure, away from its boundaries, centered at the point of symmetry in an exponential strain field is investigated here. It is assumed that the strain field is of the form $$\epsilon(x) = \epsilon^{-kx} \qquad (2.90)$$

where k is the wave number. The output of a sensor with weighting function f(x), centered at $x=0$ is then given by $$y(k) = \int_{-l/2}^{l/2} f(x) e^{-kx} dx \qquad (2.91)$$

By integrating this expression by parts repeatedly, an infinite series solution for the output of a sensor mounted in the interior of a structure, away from its boundaries, at the point of symmetry in an exponential strain field can be written as $$y(k) = \sum_{i=0}^{\infty} \frac{1}{k^{i+1}} [-f^{(i)}(l/2)e^{-kl/2} + f^{(i)}(-l/2)e^{kl/2}] \qquad (2.92)$$

Since the strain at the center of the sensor is always unity, the transfer function for such a sensor is $$T(k) = \sum_{i=0}^{\infty} \frac{1}{k^{i+1}} [-f^{(i)}(l/2)e^{-kl/2} + f^{(i)}(-l/2)e^{kl/2}] \qquad (2.93)$$

It can be seen that the transfer function has the general form of (2.40), except that the modulating functions of the $f^{(i)}(\pm \frac{1}{2})$ terms are always exponentials. Due to the definition of the strain field in 2.90, it is clear that the magnitude of the field increases with wave number k for all $x<0$. The sensor will sense this increase and consequently the output function increases exponentially. In addition, since the strain at the center of the sensor is unity for all k, the transfer function of the sensor also increases exponentially. As f(x) is made smoother at the ends, the $f^{(i)}(\pm \frac{1}{2})$ terms are zero for higher and higher values of i, and the first nonzero term will be attenuated by a smaller and smaller $1/k^{i+l}$ term. However, $e^{k\frac{l}{2}}/k^{i+l} \to \infty$ as $k \to \infty$ for any value of i because all derivatives of the numerator $e^{k\frac{l}{2}}$ increase with k, while the (i+2)-nd derivative of $k^{i+l}$ is zero.

Next the output of a sensor mounted in the interior of a structure, away from its boundaries, centered at a distance $x_o$ from the point of symmetry in an exponential strain field is described. It is assumed that the strain field is of the form $$\epsilon(x) = \epsilon^{-kx} \qquad (2.94)$$

where k is the wave number. The output of a sensor with weighting function f(x), centered at $x=x_o$ is then given by $$y(k) = \int_{-l/2 + x_0}^{l/2 + x_0} f(x - x_0) e^{-kx} dx \qquad (2.95)$$

By repeated integration by parts of this expression, an infinite series solution for the output of a sensor mounted in the interior of a structure, away from its boundaries, at a distance $x_o$ from the point of symmetry in an exponential strain field can be written as $$y(k) = \sum_{i=0}^{\infty} \frac{1}{k^{i+1}} [-f^{(i)}(l/2)e^{-kl/2} + f^{(i)}(-l/2)e^{kl/2}] e^{-kx_0} \qquad (2.96)$$

This expression is the same as (2.92), the output of a sensor centered at the origin, attenuated by the factor $e^{-kx_o}$. This attenuation arises from the inherent attenuation in the assumed exponential strain field. It is clear that when $x_o < \frac{1}{2}$, the output of the sensor increases exponentially by the factor $e^{k(l/2-x_0)}$ because the exponential strain field is increasing by that factor over part of the sensitive area of the sensor. When $x_o = \frac{1}{2}$, the sensor output rolls off due to the $1/k^{i+1}$ factors. Finally, when $x_o > \frac{1}{2}$, the output rolls off due not only to $1/k^{i+1}$ factors, but by the exponential $e^{k(\frac{1}{2} - x_o)}$.

In order to obtain the transfer function for a sensor centered at a distance $x_o$ from the origin of the strain field, (2.96) must be divided by $e^{-kx_o}$, the strain at the center of the sensor to obtain:

$$T(k) = \sum_{i=0}^{\infty} \frac{1}{k^{i+1}} [-f^{(i)}(l/2)e^{-kl/2} + f^{(i)}(-l/2)e^{kl/2}] \qquad (2.97)$$

This is effectively the same expression as (2.93), indicating that the transfer function of a sensor in an exponential strain field, away from the boundaries of the structure is constant, no matter where the sensor is centered with respect to the point of symmetry in the strain field. Note that the sensor does not have to be symmetric for this to be true, unlike the case for a sinusoidal strain field.

Now the output of a sensor mounted near a boundary of a structure, at a distance $z_o$ from the point of symmetry in an exponential strain field is investigated. This case is extremely important as it simulates the behavior of a sensor truncated at the boundary of a structure with an evanescent exponential strain field. Examples of such strain fields include the modeshapes of clamped-free and free-free beams. For this problem, it is again assumed that the strain field is of the form $$\epsilon(\chi) = e^{-k\chi} \tag{2.98}$$

where k is a parameter that depends on mode number. It is assumed that the boundary of a structure is at $x=0$. The output of a sensor with weighting function $f(x)$, centered at $x = x_o$ is then given by $$y(k) = \int_0^{l/2 + x_0} f(x - x_0) e^{-kx} dx \tag{2.99}$$

Again, an infinite series solution for the output of a sensor mounted near a boundary of a structure, at a distance $x_o$ from the point of symmetry in an exponential strain field can be found by repeatedly integrating this expression by parts:

$$y(k) = \sum_{i=0}^{\infty} \frac{1}{k^{i+1}} [-f^{(i)}(l/2) e^{-k(l/2 + x_0)} + f^{(i)}(-x_0)] \tag{2.100}$$

It is assumed that the truncated sensor is centered somewhere in the interior of the structure. This guarantees that $l/2 > x_o > 0$. Thus $l/2 + x_o$ is positive and the factor $e^{-k(l/2 + x_o)}$ is an attenuating one. The first term in (2.100) will therefore roll off quicker than the $f^{(i)}(-x_o)$ term, which is the value of the spatial weighting at the boundary of the structure. It was stated for the case of truncated sensors in sinusoidal strain fields that this value is, in general, nonzero. This therefore limits the rolloff rate of the sensor output to $1/k$. This behavior is very similar to the case of a sinusoidally varying strain field.

The transfer function for a sensor truncated at the boundary of the structure, in an exponential strain field is simply (2.100) divided by the strain at the sensor's center:

$$T(k) = \sum_{i=0}^{\infty} \frac{1}{k^{i+1}} [-f^{(i)}(l/2) e^{-kl/2} + f^{(i)}(-x_0) e^{kx_0}] \tag{2.101}$$

This expression suggests that while the first term still decreases in magnitude as k is increased, for any value of i, the second term instead increases as $e^{kx_0} k^{i+1}$. This is simply because the strain at the center of the sensor ($e^{-kx_0}$) decreases more rapidly than the strain at the boundary of the structure, which is unity.

As for sinusoidally varying strain fields, an effort is made here to improve the truncation technique for sensors near a structural boundary, in an exponential strain field. FIG. 24 shows the procedure used to fold and flip the truncated part of a sensor. In this section, the effect of performing this operation when the strain field is exponential rather than sinusoidal is described. The output of the modified sensor is given by $$y(k) = \int_0^{l/2 - x_0} [f(x - x_0) - f(-x - x_0)] e^{-kx} dx + \tag{2.102}$$

$$\int_{l/2 - x_0}^{l/2 + x_0} f(x - x_0) e^{-kx} dx$$

The weighting $f(-x - x_o)$ is again the original weighting $f(x - x_o)$ reflected about the boundary of the structure at $x = 0$. The length of the portion of the sensor that extends beyond the boundary of the sensor is $l/2 - x_o$. The above equation can be rewritten $$y(k) = \int_0^{l/2 + x_0} f(x - x_0) e^{-kx} dx - \tag{2.103}$$

$$\int_0^{l/2 - x_0} f(-x - x_0) e^{-kx} dx$$

$$y(k) = G(k) - H(k) \tag{2.104}$$

The first integral $G(k)$ in (2.103) was dealt with in the previous section and the result is shown in (2.100). By repeated integration by parts, $H(k)$ can be written as an infinite series in the following manner:

$$H(k) = \sum_{i=0}^{\infty} \frac{(-1)^i}{k^{i+1}} [f^{(i)}(-x_0) - f^{(i)}(-l/2) e^{-k(l/2 - x_0)}] \tag{2.105}$$

Now $G(k)$ and $H(k)$ are rewritten in slightly different forms:

$$G(k) = \sum_{i=0}^{\infty} \left\{ \frac{1}{k^{(2i+1)}} [-f^{(2i)}(l/2) e^{-k(l/2 + x_0)} + f^{(2i)}(-x_0)] + \right. \tag{2.106}$$

$$\left. \frac{1}{k^{(2i+2)}} [-f^{(2i+1)}(l/2) e^{-k(l/2 + x_0)} + f^{(2i+1)}(-x_0)] \right\}$$

$$H(k) = \sum_{i=0}^{\infty} \left\{ \frac{1}{k^{(2i+1)}} [f^{(2i)}(-x_0) - f^{(2i)}(-l/2) e^{-k(l/2 - x_0)}] + \right. \tag{2.107}$$

$$\left. \frac{1}{k^{(2i+2)}} [-f^{(2i+1)}(-x_0) + f^{(2i+1)}(-l/2) e^{-k(l/2 - x_0)}] \right\}$$

By subtracting the expression for $H(k)$ from $G(k)$ the output of the modified sensor as a function of frequency can be found:

$$y(k) = \sum_{i=0}^{\infty} \left\{ \frac{1}{k^{(2i+1)}} [-f^{(2i)}(l/2) e^{-k(l/2 + x_0)} + \right. \tag{2.108}$$

$$f^{(2i)}(-l/2) e^{-k(l/2 - x_0)}] + \frac{1}{k^{(2i+2)}} [-f^{(2i+1)}(l/2) e^{-k(l/2 + x_0)} -$$

$$\left. f^{(2i+1)}(-l/2) e^{-k(l/2 - x_0)} + 2 f^{(2i+1)}(x_0)] \right\}$$

Noting that we have $l/2 > x_o > 0$, we see that the sensor output (2.108) must roll off as k is increased, because all the exponential terms are attenuating ones;

By dividing this expression by $e^{-kx_0}$, the transfer function of the sensor is found to be $$T(k) = \sum_{i=0}^{\infty} \left\{ \frac{1}{k^{(2i+1)}} [-f^{(2i)}(l/2)e^{-kl/2} + f^{(2i)}(-l/2)e^{-k(l/2-2x_0)}] + \frac{1}{k^{(2i+2)}} [-f^{(2i+1)}(l/2)e^{-kl/2} - f^{(2i+1)}(-l/2)e^{-k(l/2-2x_0)} + 2f^{(2i+1)}(-x_0)e^{kx_0}] \right\}$$
(2.109)

As with the simple truncation scheme, we are left with the term $2f^{(2i+1)}(-x_o)e^{kx_o}/k^{(2i+2)}$, which increases exponentially as k is increased. However, this term depends on the value of the first spatial derivative of the sensor weighting at the boundary of the structure, not the value of the weighting itself. In many ways, this behavior is in similar to the same transfer function for a sinusoidal strain field.

For a centered sensor, the rolloff rate of the output and transfer function is increased as the ends of the sensor are tapered more smoothly to zero because the weighting and its derivatives are thus zero at the ends. However, note that both the output and transfer function actually increase exponentially as a function of k due to the $e^{kl/2}$ factor in the first term. This is due to the fact that the assumed strain field $e^{-kx}$ is increasing in magnitude for negative x.

For a noncentered sensor, the same rolloff behavior as for the centered sensor holds. However, note that the output y(k) will decrease when $x_o > l/2$, that is, when the entire sensor is placed on the positive x axis. This is because the strain field is everywhere decreasing with k. The transfer function will still increase exponentially, because the strain at the center of the sensor decreases much more rapidly than the strain at the end of the sensor closest to the structure boundary.

For a truncated sensor, as for a sinusoidal strain field, the rolloff rate of the output y(k) is reduced to at most 1/k no matter how large $x_o$ is because the value of the sensor weighting at the structure boundary is nonzero. For the transfer function, the exponential increase is increased as $x_o$ is increased.

For a folded sensor, the rolloff rate of the sensor output is now only limited to $1/k^2$ because the term $f(-x_o)$ is made zero. Although the transfer function still increases exponentially, it does so more slowly than for a simply truncated sensor.

What is claimed is:

1. An improved surface sensor for mounting in proximity to a surface of a structure to sense a property of the surface and produce an output for controlling the surface, such sensor being coupled to produce a sensing signal which responds primarily to said property of said surface and having a shape to produce signal weighting decreasing away from an interior region of the sensor so as to provide a spatially transformed output signal without aliasing that rolls off quickly with frequency.

2. An improved sensor according to claim 1, wherein said weighting tapers symmetrically to zero at edges of an active sensing region of said sensor.

3. An improved sensor according to claim 1, wherein the sensor is adapted for mounting at an edge of a surface, and said weighting is asymmetric.

4. An improved sensor according to claim 3, wherein the weighting is obtained from a symmetric weighting by truncation, inversion and reflection.

5. An improved sensor according to claim 1, wherein said weighting is achieved by a shaped distribution of active sensing material in said sensor.

6. An improved sensor according to claim 5, having a sensing element selected from among piezoelectric, resistive, capacitive and radiation sensitive material.

7. An improved sensor according to claim 6, wherein said sensor is a piezoelectric sensor and said weighting is achieved by a shaped electrode contact surface.

8. An improved sensor according to claim 1, wherein said weighting function is selected such that its transfer function in a sinusoidal field of said surface property and has rolloff given by $1/k^m$, where $m \geq 1$.

9. An improved sensor according to claim 1, wherein said weighting is selected such that its transfer function in an exponential field of said surface property and has rolloff faster than $1/k^m$, where $m > 1$.

10. An improved sensor according to claim 1, wherein said weighting has derivative approaching zero at edges of an active sensing region.

11. An improved sensor according to claim 1, wherein said weighting has a continuous derivative.

12. An improved sensor according to claim 1, wherein said weighting is independent of structural modes of said surface.

13. A sensor system for sensing properties of a surface, such system comprising a plurality of identical sensors each one being mounted for sensing the property over a corresponding region of the surface and developing a signal indicative thereof, and each having a weighting such that a combination of the output signals has high roll off in spatial frequency and a finite spatial transform.

14. An improved sensor for mounting a plurality of identical counterparts over a surface to sense a spatial property thereof, such sensor extending over a region and having weighting distribution decreasing outwardly from a central portion of the sensor such that a combination of output signals from said counterparts has high roll off in spatial frequency and a finite spatial transform over the structure.

15. A surface sensor having a sensing region with spatially-distributed sensitivity that responds primarily to a property of the surface and produces an output signal, the sensitivity being in accordance with a weighting function such that superpositions and combinations of plural identical such surface sensors covering a structure have finite spatial transforms over the structure and high roll off in spatial frequency.

* * * * *